US008314073B2

(12) United States Patent
Takagi et al.

(10) Patent No.: US 8,314,073 B2
(45) Date of Patent: Nov. 20, 2012

(54) CANCER-CELL-SPECIFIC CELL PROLIFERATION INHIBITORS

(75) Inventors: Motoki Takagi, Shinagawa-ku (JP); Akira Shimamoto, Horoshima (JP); Yasuhiro Furuichi, Kamakura (JP); Ayumi Sato, Yokohama (JP)

(73) Assignee: Genecare Research Institute Co., Ltd., Kamakura-shi (JP)

( * ) Notice: Subject to any disclaimer, the term of this patent is extended or adjusted under 35 U.S.C. 154(b) by 909 days.

(21) Appl. No.: 11/791,129

(22) PCT Filed: Nov. 17, 2005

(86) PCT No.: PCT/JP2005/021099
§ 371 (c)(1),
(2), (4) Date: Mar. 16, 2009

(87) PCT Pub. No.: WO2006/054625
PCT Pub. Date: May 26, 2006

(65) Prior Publication Data
US 2009/0215867 A1    Aug. 27, 2009

(30) Foreign Application Priority Data
Nov. 19, 2004   (JP) .................................. 2004-336742

(51) Int. Cl.
*C07H 21/02* (2006.01)
*C07H 21/04* (2006.01)
*A61K 31/70* (2006.01)
*C12Q 1/68* (2006.01)

(52) U.S. Cl. ..................... 514/44 A; 536/24.1; 536/23.1; 536/24.5

(58) Field of Classification Search ........................ None
See application file for complete search history.

(56) References Cited

U.S. PATENT DOCUMENTS

| 6,335,435 | B1 | 1/2002 | Shimamoto et al. |
| 6,472,513 | B1 | 10/2002 | Shimamoto et al. |
| 7,081,522 | B2 | 7/2006 | Kitao et al. |
| 2004/0224312 | A1 | 11/2004 | Kitao et al. |
| 2007/0031844 | A1* | 2/2007 | Khvorova et al. ................. 435/6 |
| 2007/0243570 | A1 | 10/2007 | Takagi et al. |
| 2009/0028861 | A1 | 1/2009 | Takagi et al. ............... 424/138.1 |
| 2010/0168209 | A1 | 7/2010 | Takagi et al. ............... 514/44 A |

FOREIGN PATENT DOCUMENTS

| JP | 11276173 | A | 10/1999 |
| JP | 2000166600 | A | 6/2000 |
| JP | 2000166600 | A1 | 6/2000 |
| WO | 9905284 | A1 | 2/1999 |
| WO | 0043522 | A1 | 7/2000 |
| WO | 02068590 | A2 | 9/2002 |
| WO | 2004100990 | A1 | 11/2004 |
| WO | 2005097189 | A1 | 10/2005 |

OTHER PUBLICATIONS

Brummelkamp et al., Science vol. 296:550-553, 2002.*
Brosh, Jr., Robert M. et al., Werner syndrome protein interacts with human flap endonuclease 1 and stimulates its cleavage activity, The EMBO Journal, 2001, 5791-5801, vol. 20, No. 20, Oxford University Press.
Doe, Claudette L. et al., Partial suppression of the fission yeast rqh1-phenotype by expression of a bacterial Holliday junction resolvase, The EMBO Journal, 2000, 2751-2762, vol. 19, No. 11, European Molecular Biology Organization.
Ellis, Nathan A. et al., The Bloom's Syndrome Gene Product Is Homologous to RecQ Helicases, Cell, Nov. 17, 1995, 655-666, vol. 83, Cell Press.
Ellis, Nathan A. et al., Molecular genetics of Bloom's syndrome, Human Molecular Genetics, 1996, 1457-1463, vol. 5, Oxford University Press.
Goto, Makoto, Hierarchical deterioration of body systems in Werner's syndrome: Implications for normal ageing, Mechanisms of Ageing and Development, Dec. 1997, 239-254, vol. 98, Elsevier Science Ireland Ltd.
Hanada, Katsuhrio et al., RecQ DNA helicase is a suppressor of illegitimate recombinations in *Escherichia coli*, PNAS, Apr. 1997, 3860-3865, vol. 94, The National Academy of Sciences of the USA.
Jeong, Yun Seong et al., Deficiency of *Caenorhabditis elegans* RecQ5 homologue reduces life span and increases sensitivity to ionizing radiation, DNA Repair, 2003, 1309-1319, vol. 2, Elsevier B.V.
Johnson, F. Brad et al., Association of the Bloom Syndrome Protein with Toposiomerase IIIα in Somatic and Meiotic Cells, Cancer Research, Mar. 1, 2000, 1162-1167, vol. 60.
Kawabe, Tamae et al., Differential regulation of human RecQ family helicases in cell transformation and cell cycle, Oncogene, 2000, 4764-4772, vol. 19, Macmillan Publishers Ltd.
Kitao, Saori et al., Cloning of Two New Human Helicase Genes of the RecQ Family: Biological Significance of Multiple Species in Higher Eukaryotes, Genomics, 1998, 443-452, vol. 54, Academic Press.
Kitao, Saori et al., Mutations in the RECQL4 cause a subset of cases of Rothmund-Thomson syndrome, Nature Genetics, May 1999, 82-84, vol. 22.
Leroy, Gary et al., Identification of RecQL1 as a Holliday junction processing enzyme in human cell lines, Nucleic Acids Research, Oct. 31, 2005, 6251-6257, vol. 33, No. 19, Oxford University Press.
Lindor, Noralane M. et al., Rothmund-Thomson syndrome in siblings: evidence for acquired in vivo mosaicism, Clinical Genetics, 1996, 124-129, vol. 49, Munksgaard.
Mohaghegh, Payam et al., The Bloom's and Werner's syndrome proteins are DNA structure-specific helicases, Nucleic Acids Research, 2001, 2843-2849, vol. 29, No. 13, Oxford University Press.

(Continued)

*Primary Examiner* — Sean McGarry
(74) *Attorney, Agent, or Firm* — Seed IP Law Group PLLC

(57) ABSTRACT

The present inventors discovered that although suppressing expression of the RecQ1 gene, a RecQ helicase family gene, shows suppressive effects on cell proliferation in cancer cells, such effects are not observed in human TIG3 cells (a normal diploid fibroblast cell line), which are normal cells. Hence, the present inventors discovered that siRNAs against RecQ1 gene have cancer cell-specific cell proliferation-suppressing effects that are mediated by suppression of the expression of said gene.

5 Claims, 6 Drawing Sheets

OTHER PUBLICATIONS

Myung, Kyungjae et al., SGS1, the *Saccharomyces cerevisiae* homologue of BLM and WRN, suppresses genome instability and homeologous recombination, Nature Genetics, Jan. 2001, 113-116, vol. 27, Nature Publishing Group.

Nakayama, Hiroaki et al., Isolation and genetic characterization of a thymineless death-resistant mutant of *Escherichia coli* K12: Identification of a new mutation (recQ1) that blocks the RecF recombination pathway, MGG, 1984, 474-480, vol. 195, Springer-Verlag.

Reynolds, Angela et al., Rational siRNA design for RNA interference, Nature Biotechnology, Mar. 2004, 326-330, vol. 22, No. 3.

Sakamoto, Shuichi et al., Werner helicase relocates into nuclear foci in response to DNA damaging agents and co-localizes with RPA and Rad51, Genes to Cells, 2001, 421-430, vol. 6, Blackwell Science Limited.

Seki, Masayuki et al., Molecular cloning of cDNA encoding human DNA helicase Q1 which has homology to *Escherichia coli* Rec Q helicase and localization of the gene at chromosome 12p12, Nucleic Acids Research, 1994, 4566-4573, vol. 22, No. 22, Oxford University Press.

Sharma, Sudha et al., Mechanisms of RecQ helicases in pathways of DNA metabolism and maintenance of genomic stability, Biochem. J, 2006, 319-337, vol. 398, Biochemical Society.

Sharma, Sudha et al., RECQL, a Member of the RecQ Family of DNA Helicases, Suppresses Chromosomal Instability, Molecular and Cellular Biology, Mar. 2007, 1784-1794, American Society for Microbiology.

Sugimoto, Masanobu et al., Incorrect Use of "Immortalization" for B-Lymphoblastoid Cell Lines Transformed by Epstein-Barr Virus, Journal of Virology, Nov. 1999, 9690-9691, vol. 73, No. 11, American Society for Microbiology.

Tahara, Hidetoshi et al., Abnormal telomere dynamics of B-lymphoblastoid cell strains from Werner's syndrome patients transformed by Epstein-Barr virus, Oncogene, 1997, 1911-1920, vol. 15, Stockton Press.

Wu, Leonard et al., Potential Role for the BLM Helicase in Recombinational Repair via a Conserved Interaction with RAD51, The Journal of Biological Chemistry, 2001, 19375-19381, vol. 276, No. 22, JBC Papers in Press.

Yannone, Steven M. et al., Werner Syndrome Protein is Regulated and Phosphorylated by DNA-dependant Protein Kinase, The Journal of Biological Chemistry, 2001, 38242-38248, vol. 276, No. 41, JBC Papers in Press.

Yu, Chang-En et al., Positional Cloning of the Wener's Syndrome Gene, Science, Apr. 12, 1996, 256-262, vol. 272.

Bohr, "Werner Syndrome and its Protein: Clinical, Cellular and Molecular Advances," Mechanisms of Ageing and Development 124(10-12):1073-1082, Dec. 2003.

Stein et al., "Analysis of the Role of RecQ Helicases in RNAi in Mammals," Biochemical and Biophysical Research Communications 291:1119-1122, Jan. 1, 2002.

U.S. Appl. No. 13/473,328, filed May 16, 2012, entitled "Cancer Cell-Specific Apoptosis-Inducing Agents That Target Chromosome Stabilization-Associated Genes," 182 pages.

* cited by examiner

|    | siRNA SEQUENCE       | SEQ ID NO |
|----|----------------------|-----------|
| 1  | CUACGGCUUUGGAGAUAUA  | 1         |
| 2  | GAACUGGAUUCUAUAACCA  | 2         |
| 3  | UUACCAGUUACCAGCAUUA  | 3         |
| 4  | UGAGGUUUGUUAUCCAUCA  | 4         |
| 5  | AAAUGGUCAGCCAAUGAAA  | 5         |
| 6  | GAGGAACUGGAUUCUAUAA  | 6         |
| 7  | GCAACCAUGUUAAAUGCUU  | 7         |
| 8  | GGAGCAUGUUAAAUGGGUU  | 8         |
| 9  | GCCCUCAAACACUGAAGAU  | 9         |
| 10 | GGUAGUAGUGGCAACUGUU  | 10        |
| 11 | GCAGUCUGGUUCUAAGAAU  | 11        |
| 12 | GCCCAUUGAUCUCUCUUAU  | 12        |
| 13 | GGAAUUCAUGCAGGUGCUU  | 13        |
| 14 | GGGAAUUGAUAAGCCAGAU  | 14        |
| 15 | GGAACUCAGAAGCAUGUAA  | 15        |
| 16 | GACACCGGACAGUCAAACA  | 16        |
| 17 | GUCAAACACCGGAGAGUUA  | 17        |
| 18 | GGCCACCAAAGCCUGUUUA  | 18        |
| 19 | GGAAGACCAAUUAAUGGUU  | 19        |
| 20 | CGAGUUAAAGCUGAUUUAU  | 20        |
| 21 | CGGCAGAAGCCCUCAAACA  | 21        |
| 22 | GAUAUUGUAAAGCUCAUUA  | 22        |
| 23 | CAUUAAUGGGAGAUACAAA  | 23        |
| 24 | GGGCAAUCAGGAAUCAUAU  | 24        |
| 25 | GAACAAGUUACGGUUAGUU  | 25        |
| 26 | CAGGUCGAGAUGACAUGAA  | 26        |
| 27 | CUCAGAAGCAUGUAACAAA  | 27        |
| 28 | GCAGAGAUCUAAUCAAGAU  | 28        |
| 29 | CAUACAAUCGUCUUAAGUU  | 29        |
| 30 | CAUGGUCUGGUAAAGUUAA  | 30        |
| 31 | GGCUCAACAUUUUGAUGAA  | 31        |
| 32 | GGUUCAUGCUGAAAUGGUA  | 32        |

FIG. 1

|    | GENE EXPRESSION LEVEL |
|----|----|
| 1  | 3%  |
| 2  | 14% |
| 3  | 13% |
| 4  | 8%  |
| 5  | 12% |
| 6  | 24% |
| 7  | 8%  |
| 8  | 5%  |
| 9  | 4%  |
| 10 | 3%  |
| 11 | 7%  |
| 12 | 3%  |
| 13 | 8%  |
| 14 | 4%  |
| 15 | 2%  |
| 16 | 31% |
| 17 | 31% |
| 18 | 24% |
| 19 | 25% |
| 20 | 13% |
| 21 | 4%  |
| 22 | 7%  |
| 23 | 4%  |
| 24 | 2%  |
| 25 | 5%  |
| 26 | 31% |
| 27 | 14% |
| 28 | 13% |
| 29 | 33% |
| 30 | 8%  |
| 31 | 7%  |
| 32 | 5%  |

FIG. 2

|    | SURVIVAL RATE |
|----|---------------|
| 1  | 65% |
| 2  | 31% |
| 3  | 3%  |
| 4  | 70% |
| 5  | 43% |
| 6  | 19% |
| 7  | 58% |
| 8  | 70% |
| 9  | 0%  |
| 10 | 55% |
| 11 | 31% |
| 12 | 37% |
| 13 | 23% |
| 14 | 1%  |
| 15 | 0%  |
| 16 | 14% |
| 17 | 29% |
| 18 | 63% |
| 19 | 74% |
| 20 | 42% |
| 21 | 22% |
| 22 | 47% |
| 23 | 20% |
| 24 | 10% |
| 25 | 58% |
| 26 | 31% |
| 27 | 21% |
| 28 | 21% |
| 29 | 66% |
| 30 | 57% |
| 31 | 71% |
| 32 | 34% |

FIG. 3 ern filing of PCT/JP2005/021099, International filing date of Nov. 17, 2005, which application claims priority to Japanese Application No. 2004-336742, filed Nov. 19, 2004.
CANCER-CELL-SPECIFIC CELL PROLIFERATION INHIBITORS

CROSS-REFERENCE TO RELATED APPLICATIONS

National Stage filing of PCT/JP2005/021099, International filing date of Nov. 17, 2005, which application claims priority to Japanese Application No. 2004-336742, filed Nov. 19, 2004.

The Sequence Listing associated with this application is provided in text format in lieu of a paper copy, and is hereby incorporated by reference into the specification. The name of the text file containing the Sequence Listing is 390081_403USPC_SEQUENCE_LISTING.txt. The text file is 30 KB, was created on Aug. 4, 2011, and is being submitted electronically via EFS-Web.

TECHNICAL FIELD

The present invention relates to compounds that suppress expression of RecQ1 genes, and particularly relates to cell proliferation inhibitors comprising siRNAs that exhibit the effect of suppressing expression of these genes.

BACKGROUND ART

Genes belonging to the RecQ DNA helicase family are widely present in organisms ranging from prokaryotes such as *Escherichia coli* (*E. coli*) to higher eukaryotes including humans. Conserved in the evolution process, these genes diversified along with the multicellularization of organisms. The *E. coli* RecQ gene was the first of the RecQ family genes to be discovered. This gene was identified as a gene participating in zygotic recombination and in the RecF pathway for UV damage repair (see Non-Patent Document 1). The *E. coli* RecQ gene has been revealed to have the function of suppressing incorrect recombinations (see Non-Patent Document 2). The budding yeast SGS1 gene and the fission yeast Rqh1 gene are the only known RecQ homologues in these yeasts. Both of these genes mainly suppress recombination and play important roles in genome stabilization (see Non-Patent Documents 3 and 4). Higher eukaryotes carry a number of RecQ homologues. In humans, there are five types of genes known to belong to the RecQ family: the RecQL1 (see Non-Patent Document 6), BLM, WRN, RTS, and RecQL5 genes. Of these five, the RTS gene (see Non-Patent Document 5 and Patent Documents 1 and 2) and the RecQL5 gene (see Non-Patent Document 5 and Patent Document 3) were identified by the present inventors. The BLM, WRN, and RTS genes respectively cause Bloom's syndrome (see Non-Patent Document 7), Werner's syndrome (see Non-Patent Document 8), and Rothmund-Thomson syndrome (see Non-Patent Document 9). These genes all play important roles in genome stabilization in cells.

In fibroblast cells and lymphocytic cell lines derived from patients with Werner's syndrome, chromosomal translocation and deletion, which are indexes for genome instability, have been reported to occur with high frequency (see Non-Patent Document 10). Chromosomal breakage and sister chromatid exchange (SCE) are frequently detected in cells derived from patients with Bloom's syndrome (see Non-Patent Document 11). Trisomies of human chromosome 2 and 8 are frequently found in lymphocytes derived from patients with Rothmund-Thomson syndrome (see Non-Patent Document 12). These findings suggest that the WRN helicase, BLM helicase, and RTS helicase encoded by the various causative genes of these three genetic diseases play important roles in genome stabilization in cells.

Telomere length abnormalities are seen in lymphocytic cell lines derived from patients with Werner's syndrome as compared to cell lines derived from normal healthy subjects (see Non-Patent Document 13). In addition, cell immortalization was not observed in lymphocytic cell lines derived from patients with Werner's syndrome, although about 15% of cell lines derived from normal healthy subjects were immortalized after passaging (see Non-Patent Document 14). This finding indicates that WRN helicase contributes to telomere structure maintenance, and is thus essential for the immortalization (canceration) of lymphocytic cell lines.

It has been suggested that WRN helicase is associated with homologous recombination-mediated repair, because the helicase forms foci in the nucleus in response to DNA-damaging agents, and these foci are co-localized with the single-stranded DNA-binding protein RPA (which is a WRN-binding protein) and with the recombination repair factor RAD51 (see Non-Patent Document 15). In addition, WRN helicase has been known to bind to the DNA-dependent protein kinase complex (DNA-PK) and to flap endonuclease 1 (FEN-1). By binding to DNA-PK, WRN helicase plays an important role in the processing of terminals generated by DNA double strand breaks, which are repaired in the pathway of non-homologous end joining (see Non-Patent Document 16). WRN helicase is believed to activate FEN-1 by binding to it, and to provide a site for precise reconstruction of the replication fork through homologous recombination by processing Okazaki fragments (see Non-Patent Document 17). The above findings suggest that WRN helicase plays an important role in DNA repair during DNA replication.

BLM helicase is localized in the PML body, a specific structure found in the nucleus, and it binds to topoisomerase III (see Non-Patent Document 18). The helicase has the unwinding activity of the G-quadruplex structure, and thus is considered to contribute to telomere maintenance (see Non-Patent Document 19). Furthermore, the helicase has been reported to unwind the Holliday junction and to interact with the Rad51 protein (see Non-Patent Document 20). These findings suggest that BLM helicase cooperates with other DNA-metabolizing enzymes and plays an important role in recombinational DNA repair and telomere maintenance.

Of the five human proteins belonging to the RecQ DNA helicase family (RecQ1, BLM, WRN, RTS, and RecQ5), RecQ1, BLM, WRN, and RTS are expressed at negligible levels in resting cells, but are expressed at high levels in cells whose proliferation has been enhanced by transformation with viruses (see Non-Patent Document 21). Furthermore, when the carcinogenic promoter TPA is added to resting cells, the expression of RecQ1, BLM, WRN, and RTS is induced along with the induction of cell division (see Non-Patent Document 21). These findings suggest the importance of the RecQ DNA helicase family in cell proliferation.

Taken collectively, these findings suggest that the RecQ DNA helicase family members may be potential target molecules for anti-cancer therapy because the family members participate in genomic repair in cells (BLM, WRN and RTS) and also in the maintenance of telomere structure (BLM and WRN), that they play important roles in the immortalization of certain cells (WRN), and that their expression is induced following cell division (RecQ1, BLM, WRN and RTS).

However, even if a compound can suppress the proliferation of cancer cells, if it has similar proliferation-suppressing effects on normal cells, that compound cannot be expected to be a useful anticancer agent. So far, nothing is known concerning how compounds that suppress expression of RecQ1 genes act on normal cells, or whether such compounds have cancer cell-specific cell proliferation-suppressing effects.

[Patent Document 1] Japanese Patent Application No. H09-200387.

[Patent Document 2] Japanese Patent Application No. H11-11218.

[Patent Document 3] Japanese Patent Application No. H10-81492 (Japanese Patent Application Kokai Publication No. (JP-A) H11-276173 (unexamined, published Japanese patent application)).

[Non-Patent Document 1] Nakayama H, Nakayama K, Nakayama R, Irino N, Nakayama Y, Hanawalt P C, "Isolation and genetic characterization of a thymineless death-resistant mutant of *Escherichia coli* K12: identification of a new mutation (recQ1) that blocks the RecF recombination pathway", Mol Gen Genet., 1984, Vol. 195, p. 474-480.

[Non-Patent Document 2] Hanada K, Ukita T, Kohno Y, Saito K, Kato J, Ikeda H, "RecQ DNA helicase is a suppressor of illegitimate recombination in *Escherichia coli*", Proc Natl Acad Sci U S A., 1997, Vol. 94, p. 3860-3865.

[Non-Patent Document 3] Myung K, Datta A, Chen C, Kolodner R D, "SGS1, the *Saccharomyces cerevisiae* homologue of BLM and WRN, suppresses genome instability and homologous recombination", Nat. Genet., 2001, Vol. 27, p. 113-116.

[Non-Patent Document 4] Doe C L, Dixon J, Osman F, Whitby M C, "Partial suppression of the fission yeast rqh1 (−) phenotype by expression of a bacterial Holliday junction resolvase", EMBO J., 2000, Vol. 19, p. 2751-2762.

[Non-Patent Document 5] Kitao S, Ohsugi I, Ichikawa K, Goto M, Furuichi Y, Shimamoto A, "Cloning of two new human helicase genes of the RecQ family: biological significance of multiple species in higher eukaryotes", Genomics., 1998, Vol. 54, p. 443-452.

[Non-Patent Document 6] Seki, M., Miyazawa, H., Tada, S., Yanagisawa, J., Yamaoka, T., Hoshino, S., Ozawa, K., Eki, T., Nogami, M., Okumura K., et al, "Molecular cloning of cDNA encoding human DNA helicase Q1 which has homology to *Escherichia coli* Rec Q helicase and localization of the gene at chromosome 12p12", Nucleic Acids Res., 1994, Vol. 22, No. 2, p. 4566-4573.

[Non-Patent Document 7] Ellis N A, Groden J, Ye T Z, Straughen J, Lennon D J, Ciocci S, Proytcheva M, German J, "The Bloom's syndrome gene product is homologous to RecQ helicases", Cell, 1995, Vol. 83, p. 655-666.

[Non-Patent Document 8] Yu C E, Oshima J, Fu Y H, Wijsman E M, Hisama F, Alisch R, Matthews S, Nakura J, Miki T, Ouais S, Martin G M, Mulligan J, Schellenberg G D, "Positional cloning of the Werner's syndrome gene", Science, 1996, Vol. 272, p. 258-262.

[Non-Patent Document 9] Kitao S, Shimamoto A, Goto M, Miller R W, Smithson W A, Lindor N M, Furuichi Y, "Mutations in RECQL4 cause a subset of cases of Rothmund-Thomson syndrome", Nat. Genet., 1999, Vol. 22, p. 82-84.

[Non-Patent Document 10] Goto M, "Hierarchical deterioration of body systems in Werner's syndrome: implications for normal ageing", Mech. Ageing Dev., 1997, Vol. 98, p. 239-254.

[Non-Patent Document 11] Ellis N A, German J, "Molecular genetics of Bloom's syndrome", Hum Mol. Genet., 1996, Vol. 5, p. 1457-1463.

[Non-Patent Document 12] Lindor N M, Devries E M, Michels V V, Schad C R, Jalal S M, Donovan K M, Smithson W A, Kvols L K, Thibodeau S N, Dewald G W, "Rothmund-Thomson syndrome in siblings: evidence for acquired in vivo mosaicism", Clin Genet., 1996, Vol. 49, p. 124-129.

[Non-Patent Document 13] Tahara H, Tokutake Y, Maeda S, Kataoka H, Watanabe T, Satoh M, Matsumoto T, Sugawara M, Ide T, Goto M, Furuichi Y, Sugimoto M, "Abnormal telomere dynamics of B-lymphoblastoid cell strains from Werner's syndrome patients transformed by Epstein-Barr virus", Oncogene, 1997, Vol. 15, p. 1911-1920.

[Non-Patent Document 14] Sugimoto M, Furuichi Y, Ide T, Goto M, "Incorrect us of "immortalization" for B-lymphoblastoid cell lines transformed by Epstein-Barr virus", Virol., 1999, Vol. 73, p. 9690-9691.

[Non-Patent Document 15] Sakamoto S, Nishikawa K, Heo S J, Goto M, Furuichi Y, Shimamoto A, "Werner helicase relocates into nuclear foci in response to DNA damaging agents and co-localizes with RPA and Rad51", Genes Cells., 2001, Vol. 6, p. 421-430.

[Non-Patent Document 16] Yannone S M, Roy S, Chan D W, Murphy M B, Huang S, Campisi J, Chen D J, "Werner syndrome protein is regulated and phosphorylated by DNA-dependent protein kinase", J Biol Chem., 2001, Vol. 276, p. 38242-38248.

[Non-Patent Document 17] Brosh R M Jr, von Kobbe C, Sommers J A, Karmakar P, Opresko P L, Piotrowski J, Dianova I, Dianov G L, Bohr V A, "Werner syndrome protein interacts with human flap endonuclease 1 and stimulates its cleavage activity", EMBO J., 2001, Vol. 20, p. 5791-5801.

[Non-Patent Document 18] Johnson F B, Lombard D B, Neff N F, Mastrangelo M A, Dewolf W, Ellis N A, Marciniak R A, Yin Y, Jaenisch R, Guarente L, "Association of the Bloom syndrome protein with topoisomerase III alpha in somatic and meiotic cells", Cancer Res., 2000, Vol. 60, p. 1162-1167.

[Non-Patent Document 19] Mohaghegh P, Karow J K, Brosh Jr R M Jr, Bohr V A, Hickson I D, "The Bloom's and Werner's syndrome proteins are DNA structure-specific helicases", Nucleic Acids Res., 2001, Vol. 29, p. 2843-2849.

[Non-Patent Document 20] Wu L, Davies S L, Levitt N C, Hickson I D, "Potential role for the BLM helicase in recombinational repair via a conserved interaction with RAD51", J Biol Chem., 2001, Vol. 276, p. 19375-19381.

[Non-Patent Document 21] Kawabe, T., Tsuyama, N., Kitao, S., Nishikawa, K., Shimamoto, A., Shiratori, M., Matsumoto, T., Anno, K., Sato, T., Mitsui, Y., Seki, M., Enomoto, T., Goto, M., Ellis, N. A., Ide, T., Furuichi, Y., and Sugimoto, M., "Differential regulation of human RecQ family helicases in cell transformation and cell cycle", Oncogene., 2000, Vol. 19, No. 41, p. 4764-4772.

DISCLOSURE OF THE INVENTION

Problems to be Solved by the Invention

The present invention was achieved in view of the above circumstances. An objective of the present invention is to provide cancer cell-specific cell proliferation inhibitors aimed at suppressing expression of RecQ1 helicase genes.

Means to Solve the Problems

The expression level of the RecQ DNA helicase family was found to be significantly high in tumor cells and methods of screening for compounds that suppress tumor growth using the suppression of expression of RecQ DNA helicase family genes as an index are known. It has also been suggested that compounds suppressing RecQ helicase gene expression may suppress cancer cell growth (see Japanese Patent Application Kokai Publication No. (JP-A) 2000-166600 (unexamined, published Japanese patent application)).

However, the relationship between suppression of RecQ1 gene expression and cancer cell-specific cell proliferation suppression has until now been unknown.

Even if a certain compound is found to have cancer cell proliferation-suppressing effects, if it is unclear whether the compound has a proliferation-suppressing effect on normal cells, that compound would not be an effective pharmaceutical. This is because when such a compound also shows a proliferation-suppressing effect on normal cells, it carries the risk of side effects. In fact, to date, findings indicating that various anticancer agents have side effects have been reported (for example, Komarov P. G. et al., Science Vol. 285, 1733-1737, 1999; Kamarova E. A. and Gudkov A. V. Biochemistry (Moscow) Vol. 65, 41-48, 2000; Botchkarev V. A. Cancer Research Vol. 60, 5002-5006, 2000). If it is possible to develop pharmaceutical agents that have cancer cell-specific cell proliferation-suppressing effects and do not act on normal cells, these agents will be expected to be very useful anticancer agents with few side effects.

The present inventors carried out dedicated research to achieve the above-mentioned objectives. The expression of genes from the RecQ DNA helicase family is known to be increased in tumor cell systems (for example, cancer cells). The present inventors used siRNAs that exhibit the effect of suppressing expression of the RecQ1 gene, which belongs to the human RecQ helicase family genes, to examine the effect of suppressing RecQ1 gene expression on cancer cell proliferation. As a result, the present inventors discovered that, although suppressing the expression of the RecQ1 gene leads to observation of cell proliferation-suppressing effects in cancer cells, such effects are not seen in human TIG3 cells (normal diploid fibroblast cell line), which are normal cells. Hence, the present inventors discovered for the first time that a cancer cell-specific cell proliferation-suppressing effect is observed as a result of suppressing RecQ1 gene expression. Therefore, the RecQ1 gene may be a target molecule for excellent carcinostatic agents with few side effects. Furthermore, the present inventors succeeded in finding siRNA molecules with cancer cell-specific cell proliferation-suppressing effects. Pharmaceutical agents comprising such molecules are expected to be effective pharmaceuticals for treating cancers with few side effects.

As described above, many of the existing anticancer agents have side effects; therefore, it would be very difficult to predict in advance that a molecule having the effect of suppressing cancer cell proliferation will not act on normal cells, similarly to the siRNA molecules of the present application against the RecQ1 gene. Therefore, the siRNA molecules provided by the present invention have advantageous effects (cell proliferation-suppressing effects that are specific to cancer cells and do not affect normal cells) that cannot be predicted even by those skilled in the art.

Thus, the present invention relates to cancer cell-specific cell proliferation inhibitors that target RecQ1 helicase gene expression, and particularly relates to cancer cell-specific cell proliferation inhibitors comprising siRNAs with the effect of suppressing RecQ1 gene expression. More specifically, the present invention provides the following:

[1] a double-stranded RNA that can suppress the expression of an RecQ1 gene by an RNAi effect, wherein the RNA comprises a structure in which an RNA comprising the nucleotide sequence of any one of SEQ ID NOs: 1 to 32 or SEQ ID NOs: 40 to 43 and an RNA comprising a sequence complementary to said RNA are hybridized;

[2] the double-stranded RNA of [1], which comprises a structure in which one or more DNAs or RNAs overhang at an end;

[3] a DNA vector that can express an RNA comprising the nucleotide sequence of any one of SEQ ID NOs: 1 to 32 or SEQ ID NOs: 40 to 43;

[4] a cancer cell-specific cell proliferation inhibitor which comprises the RNA of [1] or [2], or the DNA of [3]; and

[5] an anticancer agent comprising the cancer cell-specific cell proliferation inhibitor of [4] as an active ingredient. The above-mentioned cancer cells preferably refer to human cancer cells (cancer cells of human origin).

Furthermore, the present invention relates to:

[6] a method for suppressing cell proliferation cancer cell-specifically (a method for treating a cancer), which comprises the step of administering the RNA of [1] or [2] or the DNA of [3] to an individual (a subject, test subject, patient, etc.); and

[7] a use of the RNA of [1] or [2] or the DNA of [3] in the production of a cancer cell-specific anticancer agent (a cancer cell-specific cell proliferation inhibitor).

BRIEF DESCRIPTION OF THE DRAWINGS

FIG. 1 shows the nucleotide sequences of the siRNAs against RecQ1 gene that were used in the Examples. All of the sequences are RNAs, and the overhang sequence of all of the siRNAs is the deoxynucleotides 'TT'.

FIG. 2 shows the expression levels of the RecQ1 gene in HeLa cells into which siRNAs against the RecQ1 gene have been introduced.

FIG. 3 shows the survival rates of HeLa cells 96 hours after siRNAs against the RecQ1 gene have been introduced.

BEST MODE FOR CARRYING OUT THE INVENTION

Figure 4:
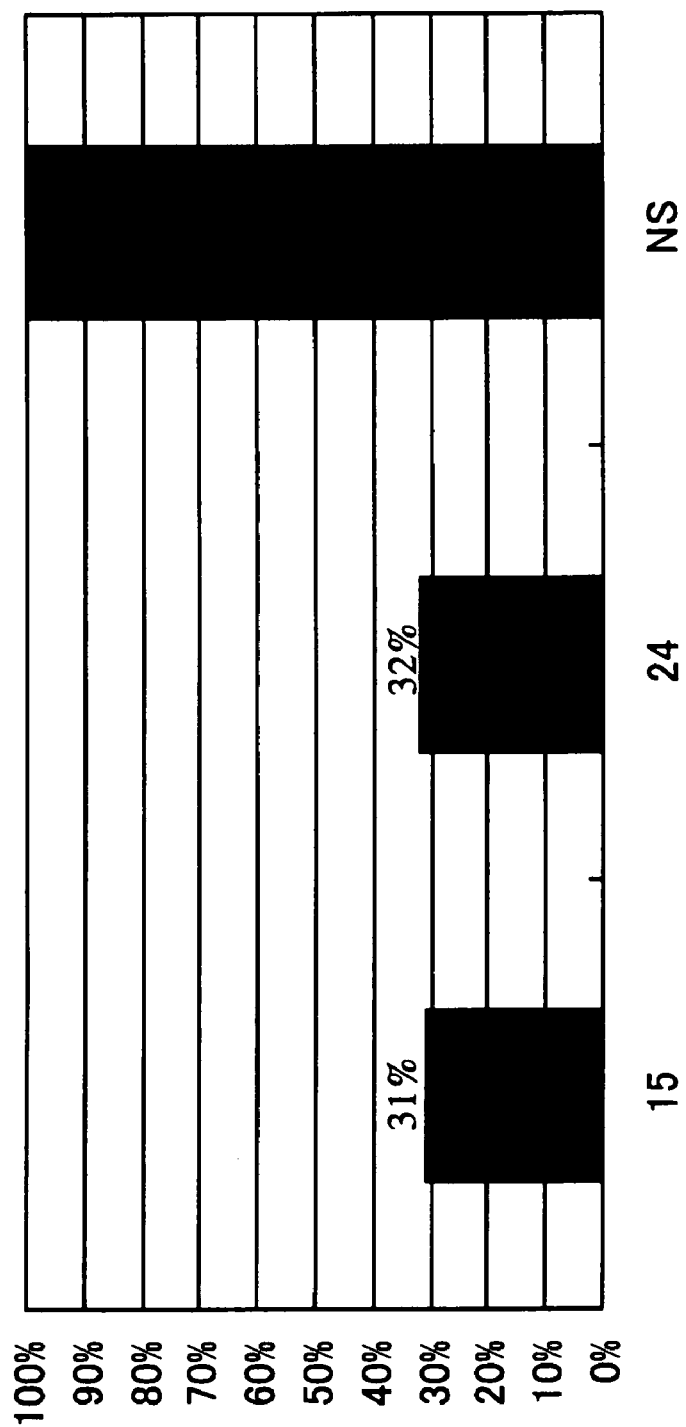
FIG. 4 is a graph showing results of introducing siRNAs against the RecQ1 gene into TIG3 cells, and then quantifying the expression of mRNAs 48 hours later by semi-quantitative RT-PCR. NS is a control siRNA. 15 and 24 are the SEQ ID NOs of siRNAs shown in FIG. 1. The gene expression obtained when a non-silencing siRNA was introduced was taken as 100%.

The present inventors discovered that, by suppressing the expression of the RecQ1 gene, which belongs to the RecQ DNA helicase family genes, cell proliferation is suppressed cancer cell (tumor cell)-specifically. Further, the present inventors discovered RNA molecules that exhibit effective cancer cell-specific cell proliferation-suppressing effects through the suppression of RecQ1 gene expression by RNAi effects.

Therefore, firstly, the present invention provides RNAs (siRNAs and shRNAs) that can suppress RecQ1 gene expression by RNAi effects. Such RNAs have cancer cell-specific cell proliferation-suppressing effects. In the present invention, the term "cancer cell-specific" refers to action against cancer cells but substantial inaction (not showing effective action) against normal cells. Cases in which the effect against normal cells is significantly less than the effect against cancer cells are also comprised in the term "cancer cell-specific" of the present invention.

Those skilled in the art can readily obtain information on the nucleotide sequences of the RecQ1 genes of the present invention from public gene databases (for example, GenBank). Exemplary GenBank accession numbers of the genes described above are listed below:

RecQ1 gene: NM_002907 (SEQ ID NO: 33), NM_032941 (SEQ ID NO: 34), BC001052 (SEQ ID NO: 35), D37984 (SEQ ID NO: 36), and L36140 (SEQ ID NO: 37).

An example of an amino acid sequence of a protein encoded by a RecQ1 gene of the present invention is indicated in SEQ ID NO: 38.

The RecQ1 genes of the present invention typically include, but are not limited to, those derived from animals, more preferably those derived from mammals, and most preferably those derived from humans.

The RNAs of the present invention that can suppress the expression of RecQ1 genes by RNAi (RNA interference) effects (may be simply referred to as "the siRNAs of the present invention" in this application) are more specifically, for example, RNAs comprising the nucleotide sequence of any one of SEQ ID NOs: 1 to 32. Furthermore, examples of preferred embodiments of the siRNAs of the present invention include double-stranded RNAs (siRNAs) that include RNAs comprising the nucleotide sequence of any one of SEQ ID NOs: 1 to 32 as one of the strands.

The present invention provides double-stranded RNAs which are RNAs (siRNAs) that can suppress RecQ1 gene expression by RNAi effects, and which comprise structures in which an RNA comprising the nucleotide sequence of any one of SEQ ID NOs: 1 to 32 and an RNA comprising a sequence complementary to this RNA are hybridized.

For example, the siRNAs of the present invention that comprise the nucleotide sequence of SEQ ID NO: 1 (5'-cuacggcuuuggagauaua-3') may be RNA molecules structured as below:

```
5'-cuacggcuuuggagauaua-3'    (SEQ ID NO: 1)
   IIIIIIIIIIIIIIIIIII
3'-gaugccgaaaccucuauau-5'    (SEQ ID NO: 39)
```

(herein, "I" indicates a hydrogen bond).

The above-mentioned RNA molecules that are structured such that one end is closed, for example, siRNAs comprising a hairpin structure (shRNAs), are also included in the present invention. Hence, molecules that can form an intramolecular double-stranded RNA structure are also comprised in the present invention.

For example, molecules such as 5'-cuacggcuuuggagauaua-3' (SEQ ID NO: 1) (xxxx)n uauaucuccaaagccguag (SEQ ID NO: 39)-3' are also comprised in the present invention. (The aforementioned "(xxxx)n" indicates a polynucleotide comprising any nucleotide and any number of sequences.)

Preferred embodiments of the siRNAs of the present invention are preferably double-stranded RNAs which are RNAs (siRNAs) that can suppress RecQ1 gene expression by RNAi effects, and which comprise a structure in which an RNA comprising the nucleotide sequence of any one of SEQ ID NOs: 1 to 32 and an RNA comprising a sequence complementary to this RNA are hybridized. Double-stranded RNAs structured such that, for example, there are one or more RNA additions or deletions at the end of such a double-stranded RNA are also comprised in the present invention. In such cases, the RNAs forming the double strand are preferably homologous to a partial sequence of a RecQ1 gene. The length of the region of the RNA forming a double strand in an siRNA of the present invention is ordinarily 15 to 30 bp, preferably 15 to 27 bp or so, more preferably 19 to 21 bp, and most preferably 19 bp (for example, an siRNA in which one of the strands is an RNA of any one of SEQ ID NOs: 1 to 32), but the length is not necessarily limited thereto.

All of the nucleotides in the siRNAs of the present invention are not necessarily required to be ribonucleotides (RNAs). Namely, in the present invention, one or more of the ribonucleotides composing the siRNAs may be corresponding deoxyribonucleotides. "Corresponding" means that the nucleotides have identical base species (adenine, guanine, cytosine, and thymine (uracil)), but that the structure of the sugar portion is different. For example, the deoxyribonucleotide corresponding to a ribonucleotide with adenine means a deoxyribonucleotide with adenine. In addition, the above "more" is not limited to a particular number but preferably means a small number around two to five.

In general, the term "RNAi" refers to a phenomenon where target gene expression is inhibited by inducing disruption of the target gene mRNAs. This disruption is caused by introducing into cells a double-stranded RNA that comprises, a) a sense RNA comprising a sequence homologous to a target gene mRNA sequence, and b) an antisense RNA comprising a sequence complementary to the sense RNA. While the precise RNAi mechanism remains unclear, it is thought that an enzyme called DICER (a member of the RNase III nuclease family) contacts the double-stranded RNA, degrading it into small fragments called "small interfering RNAs" or "siRNAs". The double-stranded RNAs of the present invention comprising the RNAi effects preferably refer to these siRNAs.

In a preferred embodiment of the present invention, the double-stranded RNAs are RNAs that can suppress RecQ1 gene expression by RNAi effects and that comprise a structure in which an RNA comprising the nucleotide sequence of any one of SEQ ID NOs: 1 to 32 and an RNA comprising a sequence complementary to this RNA are hybridized.

Furthermore, DNAs that allow the expression of the siRNAs (double-stranded RNAs) of the present invention are also included in the present invention. Specifically, the present invention provides DNAs (vectors) that allow the expression of double-stranded RNAs of the present invention. These DNAs (vectors) that allow the expression of double-stranded RNAs of the present invention are typically DNAs comprising a structure where a DNA encoding one strand of the double-stranded RNA and a DNA encoding the other strand of the double-stranded RNA are operably linked to a promoter. Those skilled in the art can readily prepare an above-described DNA of the present invention with common genetic engineering techniques. More specifically, expression vectors of the present invention can be prepared by appropriately inserting DNAs encoding RNAs of the present invention into various known expression vectors.

Generally, the double-stranded RNAs having an RNAi effect are double-stranded RNAs comprising a sense RNA, which comprises a sequence homologous to a continuous RNA region in the mRNA of a target gene whose expression is to be suppressed, and an antisense RNA, which comprises a sequence complementary to the sense RNA.

In general, since double-stranded RNAs with an overhang of several nucleotides on one end have strong RNAi effects, the double-stranded RNAs of the present invention preferably comprise an overhang of several nucleotides on an end. The length of the nucleotides forming the overhang as well as the sequence are not particularly limited. This overhang may be DNA or RNA. For example, the overhang preferably has two nucleotides. A double-stranded RNA comprising an overhang of, for example, TT (a thymine doublet), UU (a uracil doublet), or some other nucleotide (most preferably, a molecule comprising a double-stranded RNA of 19 nucleotides and an overhang of two nucleotides (TT)) can be suitably used in the present invention. The double-stranded RNAs of the present invention also include molecules in which the overhanging nucleotides are DNAs.

Examples of the siRNA molecules of the present invention where the nucleotides of the overhang portion are TT include molecules having TT added to their 3' side, such as the molecule indicated below:

```
5'-cuacggcuuuggagauauaTT-3' (SEQ ID NO: 1 + "TT" )
   ||||||||||||||||||||
3'-TTgaugccgaaaccucuauau-5' (SEQ ID NO: 39 + "TT" )
```

The above-mentioned "double-stranded RNAs having an RNAi effect on RecQ1 genes" of the present invention can be suitably produced by those skilled in the art based on the nucleotide sequences disclosed in the present description. Specifically, the double-stranded RNAs of the present invention can be produced based on the nucleotide sequence of any one of SEQ ID NOs: 1 to 32. If one of the strands has been determined (for example, a nucleotide sequence described in any one of SEQ ID NOs: 1 to 32), the nucleotide sequence of the other strand (the complementary strand) can be easily determined by those skilled in the art. siRNAs of the present invention can be suitably produced by those skilled in the art using commercially available nucleic acid synthesizers. Common custom synthesis services can also be used to synthesize desired RNAs.

Since the siRNAs of the present invention (for example, a double-stranded RNA molecule in which one of the strands has the nucleotide sequence of any one of SEQ ID NOs: 1 to 32) have cancer cell-specific cell proliferation-suppressing effects, the present invention provides cancer cell-specific cell proliferation inhibitors that comprise an siRNA of the present invention as an active ingredient.

If the cancer cell proliferation-suppressing effect in the present invention arises from the induction of apoptosis, the siRNAs of the present invention will be expected to be cancer cell-specific apoptosis-inducing agents.

The term "apoptosis" generally refers to cell death actively induced by the cell itself under physiological condition. The morphological features of apoptosis include, for example, chromosome condensation in the cell nucleus, nuclear fragmentation, loss of microvilli on the cell surface, and cytoplasmic shrinkage. Thus, as used herein, the term "apoptosis-inducing effect" refers to, for example, the effect of inducing in cells the above-described morphological features of apoptosis, but is not limited to those described above. One skilled in the art can appropriately assess whether or not apoptosis is being induced in cells.

For example, the present invention's apoptosis inducers specific for cancer cells are expected to be anticancer agents (carcinostatic agents) having apoptosis-inducing activity as their mechanism of action.

The present invention provides anticancer agents (pharmaceutical compositions for cancer therapy) that comprise a cancer cell-specific cell proliferation inhibitor of the present invention as an active ingredient.

Pharmaceutical agents of the present invention can be provided as a mixture with a pharmaceutically acceptable carrier. Such pharmaceutically acceptable carriers can include, but are not limited to, for example, detergents, excipients, coloring agents, flavoring agents, preservatives, stabilizers, buffers, suspensions, isotonizing agents, binders, disintegrating agents, lubricants, fluidizing agents, and correctives. Other conventional carriers can be also used appropriately.

The pharmaceutical agents of the present invention can be formulated by adding the above-indicated carriers as required and according to conventional methods. Specifically, such carriers include: light anhydrous silicic acid, lactose, crystalline cellulose, mannitol, starch, carmellose calcium, carmellose sodium, hydroxypropyl cellulose, hydroxypropylmethyl cellulose, polyvinylacetaldiethylamino acetate, polyvinylpyrrolidone, gelatin, medium-chain fatty acid triglyceride, polyoxyethylene hydrogenated castor oil 60, saccharose, carboxymethyl cellulose, cornstarch, and inorganic salts.

The dosage forms for the agents described above include, for example, oral forms, such as tablets, powders, pills, dispersing agents, granules, fine granules, soft and hard capsules, film-coated tablets, pellets, sublingual tablets, and pastes; and parenteral forms, such as injections, suppositories, endermic liniments, ointments, plasters, and liquids for external use. Those skilled in the art can select the optimal dosage form depending on the administration route, subject, and such.

Viral vectors such as retroviruses, adenoviruses, and Sendai viruses and non-viral vectors such as liposomes can be used to administer DNAs expressing the siRNAs of the present invention that suppress the RecQ1 genes into living bodies. Alternatively, non-viral vectors such as liposomes, polymer micelles, or cationic carriers, may be used to administer synthetic siRNAs of the present invention that suppress the RecQ1 genes into living bodies. The administration methods include, for example, in-vivo and ex-vivo methods.

The present invention also comprises the above-described pharmaceutical compositions having cancer cell-specific cell proliferation-suppressing effect. Ultimately, the doses of the pharmaceutical agents or pharmaceutical compositions of the present invention can be appropriately determined by a physician considering the type of dosage form, administration method, patient's age, weight, symptoms, and so on.

The types of cancers for which a cell proliferation-suppressing effect is expected in the present invention are not particularly limited, but examples include breast cancers, lung cancers, osteosarcomas, cervical cancers, fibrosarcomas, ovarian teratocarcinomas, embryonal cancers, bladder cancers, chronic myeloid leukemias, acute lymphoblastic leukemias, glioblastomas, liver cancers, glioblastomas, melanomas, kidney cancers, pancreatic cancers, stomach cancers, prostate cancers, and such.

Furthermore, the present invention relates to methods for suppressing cancer cell-specifically (cancer cell-specific methods for treating cancer) and methods for suppressing cell proliferation cancer cell-specifically, which comprise the step of administering an RNA or DNA of the present invention or a pharmaceutical agent of the present invention to individuals (for example, patients) or to cellular tissues (cancer cell tissues and such).

The individuals in the methods of the present invention are preferably humans, but are not particularly limited thereto, and they may be non-human animals.

In general, administration to individuals can be carried out by methods known to those skilled in the art, examples of which include intra-arterial injection, intravenous injection, and subcutaneous injection. Although the dosage varies depending on the weight and age of the subject (patient and such), the administration method, and so on, suitable dosages can be appropriately selected by those skilled in the art.

Moreover, the present invention relates to the uses of the RNAs or DNAs of the present invention, or to uses of the pharmaceutical agents of the present invention, in the production of cancer cell-specific cell proliferation inhibitors or anticancer agents.

All prior art references cited herein are incorporated by reference into this description.

EXAMPLES

The present invention will be described in detail below with reference to Examples, but is not to be construed as being limited thereto.

Example 1

Cell Cultures

HeLa cells (human cervical cancer cells) were used as human cancer cells, and TIG3 cells (normal diploid fibroblast cells) were used as normal human cells. HeLa cells and TIG3 cells were cultured at 37° C. under 5% $CO_2$ using Dulbecco's modified Eagle's medium containing 10% fetal bovine serum and 50 µg/mL gentamicin.

Example 2 siRNA Design

Thirty-two siRNAs against RecQ1 gene were designed according to the method of Elbasher et al. (Elbasher, M. S. et al. Duplexes of 21-nucleotide RNAs mediate RNA interference in cultured mammalian cells. Nature 411, 494-498 (2001)) and the method of Reynolds et al. (Reynolds A. et al., Rational siRNA design for RNA-interference. Nat. Biotechnol. 3, 326-30 (2004)). FIG. 1 shows each of the siRNA sequences. The siRNAs were synthesized at Qiagen.

Example 3

Cancer Cell-Specific Cell Proliferation-Suppressing Effects Due to the Suppression of RecQ1 Gene Expression (1) Suppression of RecQ1 Gene Expression by siRNAs Cells were plated onto 24-well plates at a density of 0.8-1.5×$10^4$ cells/well 24 hours before transfection, and siRNAs were transfected under the condition of 20-50% confluency. 10 pmol of siRNA was transfected per well using Oligofectamine (Invitrogen) or Lipofectamine 2000 (Invitrogen) following the manufacturer's protocol. Expression of the RecQ1 gene mRNA 24 hours after introduction of siRNA was quantified using Taqman PCR. Specifically, total RNA was extracted from cells at 24 hours after siRNA transfection using an RNeasy Mini Kit (Qiagen). ABI PRISM 7000 Sequence Detection System (Applied Biosystems) was used for quantitative PCR. RT-PCR primers for the RecQ1 gene and β-actin gene, and TaqMan probes were purchased from Applied Biosystems. RT-PCR reactions were performed using a QuantiTect Probe RT-PCR Kit (Qiagen) according to the manual. Expression of RecQ1 mRNA was quantitatively compared using β-actin as a standard. The expression level of the RecQ1 mRNA in cells into which control siRNAs that do not affect RecQ1 gene expression had been transfected was defined as 100%, and the RecQ1 mRNA expressions in cells into which each siRNA had been introduced were compared.

(2) Cell Proliferation Assays siRNA transfection was performed under the same conditions as described above, and 96 hours later, viable cells were measured using a viable cell count reagent SF (Nakalai Tesque). The experiment was carried out at N=3, and average values were calculated. The viable cell count of cells into which control siRNA that does not affect RecQ1 gene expression was introduced was defined as 100%, and the viable cell counts for cells into which each siRNA was introduced were calculated.

(3) Results

Using HeLa cells, which are human cervical cancer cells, the effects on cell proliferation of suppression of RecQ1 gene expression by siRNAs were investigated. As a result of individually transfecting the 32 types of siRNAs against the RecQ1 gene into HeLa cells, a gene expression-suppressing effect of 70% or more was observed for all of the siRNAs (FIG. 2). Under such conditions, when the number of viable HeLa cells after 96 hours was compared to that of the NS-siRNA-treated group, a proliferation suppression of 30% or more was observed in all of the siRNA-treated groups (FIG. 3).

Figure 5:
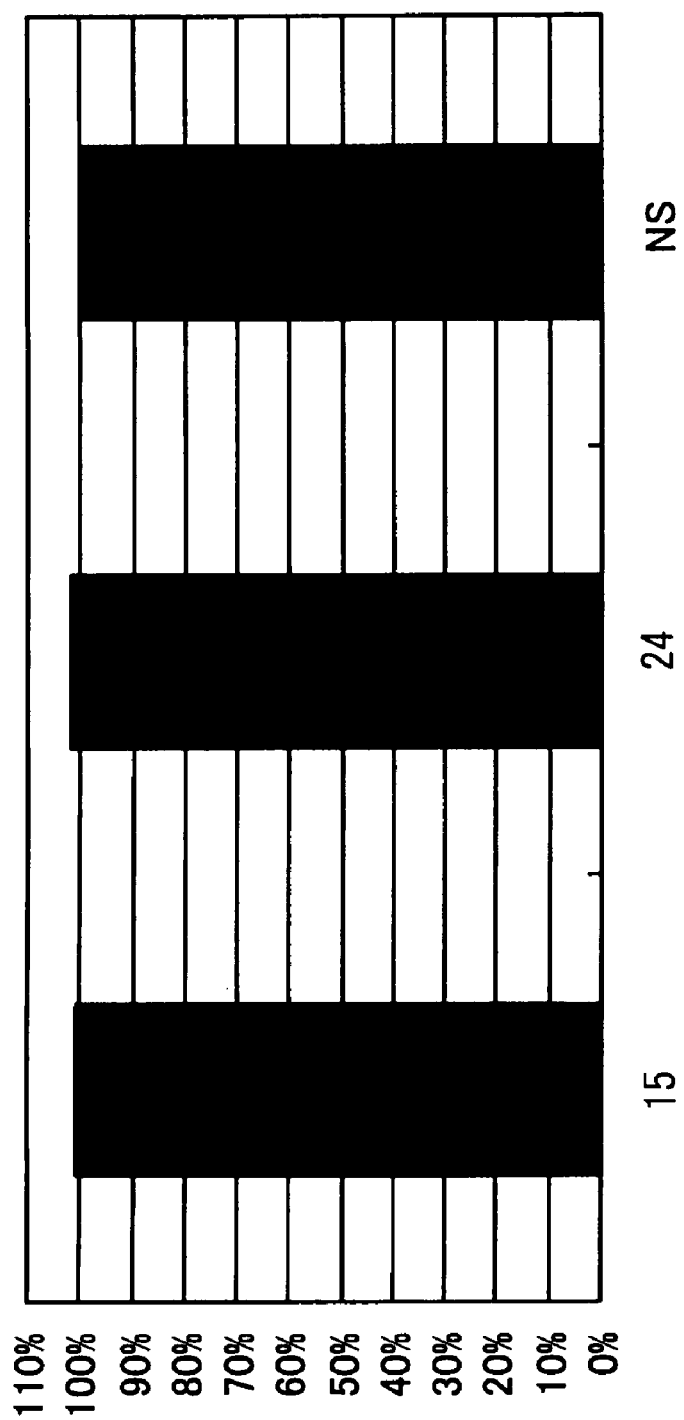
FIG. 5 is a graph indicating the survival rate of TIG3 cells 96 hours after introduction of siRNAs against the RecQ1 gene. NS is a control siRNA. 15 and 24 are the SEQ ID NOs of siRNAs shown in FIG. 1. The graph shows the number of cells when the number of cells after introduction of a non-silencing siRNA was taken as 100%.

Next, the effects on the proliferation of normal cells were investigated using TIG3 cells. When the siRNAs of SEQ ID NOs: 15 and 24, which showed strong proliferation-suppressing effects in HeLa cells, were individually introduced into TIG3 cells, each of them suppressed RecQ1 gene expression by approximately 70% (FIG. 4). Under such conditions, when the number of viable TIG3 cells after 96 hours was compared to that of the NS-siRNA-treated group, no effect on the proliferation of TIG3 cells was recognized (FIG. 5).

These results proved that RecQ1-siRNA strongly inhibits the proliferation of cancer cells, but hardly affects the proliferation of normal cells.

Example 4

Proliferation Inhibition of Tumor Cells by siRNAs in Cancer-Bearing Animal Models The sequences of the siRNAs and 27 mer dsRNA used in the animal studies are shown below:

TABLE 1

Sequences of siRNAs against RecQ1 used in animal studies

| | siRNA sequence | |
|---|---|---|
| 24 | GGGCAAUCAGGAAUCAUAU | (SEQ ID NO: 24) |
| 33 | GCUUGAAACUAUUAACGUA | (SEQ ID NO: 40) |
| 34 | UAAGACCACAGUUCAUAGA | (SEQ ID NO: 41) |
| 35 | GUUAUCCAUCAUUCAAUGA | (SEQ ID NO: 42) |

All siRNA sequences are RNAs.

The overhang sequence of all of the siRNAs is the deoxynucleotides 'TT'.

The 27 mer dsRNA sequence against RecQ1 used in animal studies

36  GGAAAAGUUCAGACCACUUCAGCUUGA (SEQ ID NO: 43)

The dsRNA sequence is all RNA and does not have an overhang.

The RecQ1 gene expression levels in HeLa cells treated with the above RecQ1-siRNAs are the following:

TABLE 2

| | Gene expression level |
|---|---|
| 33 | 3% |
| 34 | 19% |
| 35 | 18% |
| 36 | 6% |
| NS | 100% |

The present inventors also examined whether proliferation inhibition of tumor cells by siRNAs against RecQ1 helicase will also occur in cancer-bearing animal models. The siRNAs and 27 mer dsRNA against the RecQ1 gene shown above were used.

Male BALB/cA nude mice were purchased from CLEA Japan, Inc. A549 cells ($5 \times 10^6$ cells/0.1 mL) were subcutaneously transplanted into the back of nude mice (seven weeks old). siRNA administration began on the eighth day after tumor cell transplantation. With regard to RecQ1-siRNA, 22 μg of siRNA with phosphorylated 5' end was mixed with 5 μg of polyethylenimine (molecular weight of 10,000, Wako) in 50 μL of physiological saline. This mixture was subcutaneously injected six times, once every three days (on days 8, 11, 14, 17, 20, and 23), into the uppermost part of the solid tumor. The tumor volume was measured using calipers. The equation for calculating tumor volume was $L \times W^2/2$. Herein, L is the major axis and W is the minor axis of the tumor. Statistical significance of the tumor volume was analyzed using t-tests.

Figure 6:
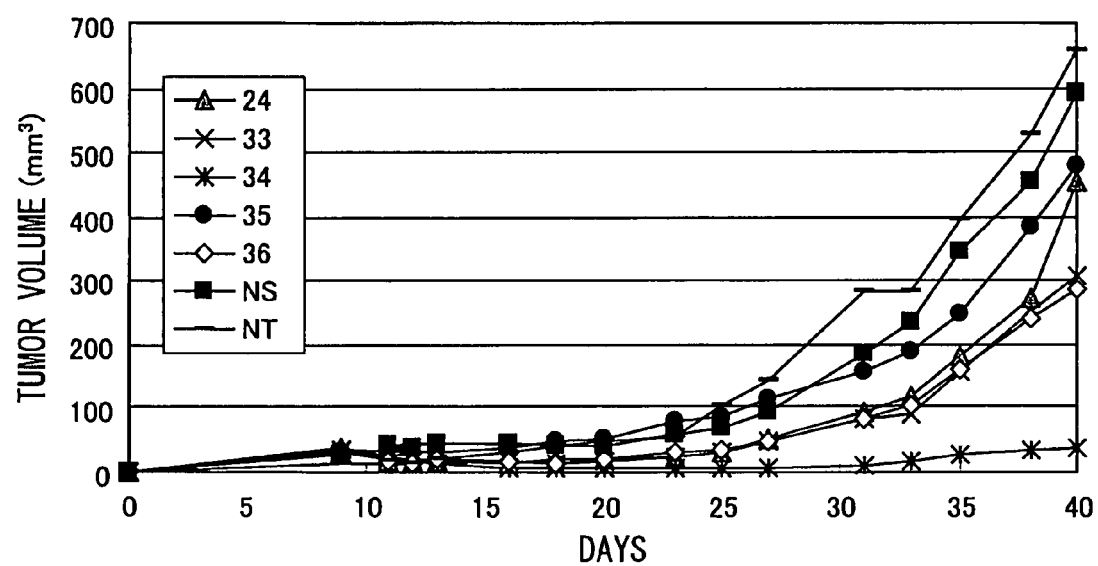
FIG. 6 shows the evaluation results of the medicinal effect of the siRNAs against the RecQ1 gene. NT refers to untreated cancer-bearing mice.

As a result, all RecQ1-siRNAs suppressed tumor growth, but NS-siRNA (an siRNA which does not affect the expression of human and mouse genes), which was similarly mixed with polyethylenimine, had no effect and tumor volume increased (FIG. 6). Mice administered with a mixture of RecQ1-siRNA and polyethylenimine did not show a reduction in weight compared to non-cancer-bearing mice, which indicated that this treatment does not have serious side effects.

The studies by the present inventors revealed that silencing of RecQ1 helicase expression causes suppression of tumors in cancer-bearing animal models.

INDUSTRIAL APPLICABILITY

Even if a certain compound is found to have the effect of suppressing cancer cell proliferation, use of that compound as a pharmaceutical is difficult when it is unclear whether it also has the effect of suppressing the proliferation of normal cells. This is because when such a compound also shows cell proliferation-suppressing effect on normal cells, it carries with it the risk of side effects. Hence, if the cell proliferation-suppressing effect is not cancer cell-specific, it would ordinarily be difficult to actually use the compound as a pharmaceutical. The pharmaceutical agents of the present invention (nucleic acids having RNAi effects) can be said to be very practical and highly effective pharmaceutical agents, since their cell proliferation-suppressing effect is cancer cell-specific.

The invention claimed is:

1. A double-stranded RNA that can suppress the expression of an RecQ1 gene by an RNAi effect, wherein the RNA comprises a structure in which an RNA comprising the nucleotide sequence of SEQ ID NO: 41 and an RNA comprising a sequence complementary to said RNA are hybridized.

2. The double-stranded RNA of claim 1, which comprises a structure in which one or more DNAs or RNAs overhang at an end.

3. A DNA vector that can express an RNA comprising the nucleotide sequence of SEQ ID NO: 41.

4. A cancer cell-specific cell proliferation inhibitor which comprises the RNA of claim 1 or 2, or the DNA of claim 3.

5. An anticancer agent comprising the cancer cell-specific cell proliferation inhibitor of claim 4 as an active ingredient.

* * * * *

SEQUENCE LISTING

```
<160> NUMBER OF SEQ ID NOS: 43

<210> SEQ ID NO 1
<211> LENGTH: 19
<212> TYPE: RNA
<213> ORGANISM: Artificial
<220> FEATURE:
<223> OTHER INFORMATION: an artificially synthesized sequence

<400> SEQUENCE: 1
cuacggcuuu ggagauaua                                              19

<210> SEQ ID NO 2
<211> LENGTH: 19
<212> TYPE: RNA
<213> ORGANISM: Artificial
<220> FEATURE:
<223> OTHER INFORMATION: an artificially synthesized sequence

<400> SEQUENCE: 2
gaacuggauu cuauaacca                                              19

<210> SEQ ID NO 3
<211> LENGTH: 19
<212> TYPE: RNA
<213> ORGANISM: Artificial
<220> FEATURE:
<223> OTHER INFORMATION: an artificially synthesized sequence
```

-continued

<400> SEQUENCE: 3
uuaccaguua ccagcauua                                          19

<210> SEQ ID NO 4
<211> LENGTH: 19
<212> TYPE: RNA
<213> ORGANISM: Artificial
<220> FEATURE:
<223> OTHER INFORMATION: an artificially synthesized sequence

<400> SEQUENCE: 4
ugagguuugu uauccauca                                          19

<210> SEQ ID NO 5
<211> LENGTH: 19
<212> TYPE: RNA
<213> ORGANISM: Artificial
<220> FEATURE:
<223> OTHER INFORMATION: an artificially synthesized sequence

<400> SEQUENCE: 5
aaauggucag ccaaugaaa                                          19

<210> SEQ ID NO 6
<211> LENGTH: 19
<212> TYPE: RNA
<213> ORGANISM: Artificial
<220> FEATURE:
<223> OTHER INFORMATION: an artificially synthesized sequence

<400> SEQUENCE: 6
gaggaacugg auucuauaa                                          19

<210> SEQ ID NO 7
<211> LENGTH: 19
<212> TYPE: RNA
<213> ORGANISM: Artificial
<220> FEATURE:
<223> OTHER INFORMATION: an artificially synthesized sequence

<400> SEQUENCE: 7
gcaaccaugu uaaaugcuu                                          19

<210> SEQ ID NO 8
<211> LENGTH: 19
<212> TYPE: RNA
<213> ORGANISM: Artificial
<220> FEATURE:
<223> OTHER INFORMATION: an artificially synthesized sequence

<400> SEQUENCE: 8
ggagcauguu aaauggguu                                          19

<210> SEQ ID NO 9
<211> LENGTH: 19
<212> TYPE: RNA
<213> ORGANISM: Artificial
<220> FEATURE:
<223> OTHER INFORMATION: an artificially synthesized sequence

<400> SEQUENCE: 9
gcccucaaac acugaagau                                          19

<210> SEQ ID NO 10
<211> LENGTH: 19

```
<212> TYPE: RNA
<213> ORGANISM: Artificial
<220> FEATURE:
<223> OTHER INFORMATION: an artificially synthesized sequence

<400> SEQUENCE: 10
gguaguagug gcaacuguu                                              19

<210> SEQ ID NO 11
<211> LENGTH: 19
<212> TYPE: RNA
<213> ORGANISM: Artificial
<220> FEATURE:
<223> OTHER INFORMATION: an artificially synthesized sequence

<400> SEQUENCE: 11
gcagucuggu ucuaagaau                                              19

<210> SEQ ID NO 12
<211> LENGTH: 19
<212> TYPE: RNA
<213> ORGANISM: Artificial
<220> FEATURE:
<223> OTHER INFORMATION: an artificially synthesized sequence

<400> SEQUENCE: 12
gcccauugau cucucuuau                                              19

<210> SEQ ID NO 13
<211> LENGTH: 19
<212> TYPE: RNA
<213> ORGANISM: Artificial
<220> FEATURE:
<223> OTHER INFORMATION: an artificially synthesized sequence

<400> SEQUENCE: 13
ggaauucaug caggugcuu                                              19

<210> SEQ ID NO 14
<211> LENGTH: 19
<212> TYPE: RNA
<213> ORGANISM: Artificial
<220> FEATURE:
<223> OTHER INFORMATION: an artificially synthesized sequence

<400> SEQUENCE: 14
gggaauugau aagccagau                                              19

<210> SEQ ID NO 15
<211> LENGTH: 19
<212> TYPE: RNA
<213> ORGANISM: Artificial
<220> FEATURE:
<223> OTHER INFORMATION: an artificially synthesized sequence

<400> SEQUENCE: 15
ggaacucaga agcauguaa                                              19

<210> SEQ ID NO 16
<211> LENGTH: 19
<212> TYPE: RNA
<213> ORGANISM: Artificial
<220> FEATURE:
<223> OTHER INFORMATION: an artificially synthesized sequence

<400> SEQUENCE: 16
gacaccggac agucaaaca                                              19
```

```
<210> SEQ ID NO 17
<211> LENGTH: 19
<212> TYPE: RNA
<213> ORGANISM: Artificial
<220> FEATURE:
<223> OTHER INFORMATION: an artificially synthesized sequence

<400> SEQUENCE: 17
gucaaacacc ggagaguua                                                      19

<210> SEQ ID NO 18
<211> LENGTH: 19
<212> TYPE: RNA
<213> ORGANISM: Artificial
<220> FEATURE:
<223> OTHER INFORMATION: an artificially synthesized sequence

<400> SEQUENCE: 18
ggccaccaaa gccuguuua                                                      19

<210> SEQ ID NO 19
<211> LENGTH: 19
<212> TYPE: RNA
<213> ORGANISM: Artificial
<220> FEATURE:
<223> OTHER INFORMATION: an artificially synthesized sequence

<400> SEQUENCE: 19
ggaagaccaa uuaaugguu                                                      19

<210> SEQ ID NO 20
<211> LENGTH: 19
<212> TYPE: RNA
<213> ORGANISM: Artificial
<220> FEATURE:
<223> OTHER INFORMATION: an artificially synthesized sequence

<400> SEQUENCE: 20
cgaguuaaag cugauuuau                                                      19

<210> SEQ ID NO 21
<211> LENGTH: 19
<212> TYPE: RNA
<213> ORGANISM: Artificial
<220> FEATURE:
<223> OTHER INFORMATION: an artificially synthesized sequence

<400> SEQUENCE: 21
cggcagaagc ccucaaaca                                                      19

<210> SEQ ID NO 22
<211> LENGTH: 19
<212> TYPE: RNA
<213> ORGANISM: Artificial
<220> FEATURE:
<223> OTHER INFORMATION: an artificially synthesized sequence

<400> SEQUENCE: 22
gauauuguaa agcucauua                                                      19

<210> SEQ ID NO 23
<211> LENGTH: 19
<212> TYPE: RNA
<213> ORGANISM: Artificial
<220> FEATURE:
<223> OTHER INFORMATION: an artificially synthesized sequence
```

```
<400> SEQUENCE: 23
cauuaauggg agauacaaa                                              19

<210> SEQ ID NO 24
<211> LENGTH: 19
<212> TYPE: RNA
<213> ORGANISM: Artificial
<220> FEATURE:
<223> OTHER INFORMATION: an artificially synthesized sequence

<400> SEQUENCE: 24
gggcaaucag gaaucauau                                              19

<210> SEQ ID NO 25
<211> LENGTH: 19
<212> TYPE: RNA
<213> ORGANISM: Artificial
<220> FEATURE:
<223> OTHER INFORMATION: an artificially synthesized sequence

<400> SEQUENCE: 25
gaacaaguua cgguuaguu                                              19

<210> SEQ ID NO 26
<211> LENGTH: 19
<212> TYPE: RNA
<213> ORGANISM: Artificial
<220> FEATURE:
<223> OTHER INFORMATION: an artificially synthesized sequence

<400> SEQUENCE: 26
caggucgaga ugacaugaa                                              19

<210> SEQ ID NO 27
<211> LENGTH: 19
<212> TYPE: RNA
<213> ORGANISM: Artificial
<220> FEATURE:
<223> OTHER INFORMATION: an artificially synthesized sequence

<400> SEQUENCE: 27
cucagaagca uguaacaaa                                              19

<210> SEQ ID NO 28
<211> LENGTH: 19
<212> TYPE: RNA
<213> ORGANISM: Artificial
<220> FEATURE:
<223> OTHER INFORMATION: an artificially synthesized sequence

<400> SEQUENCE: 28
gcagagaucu aaucaagau                                              19

<210> SEQ ID NO 29
<211> LENGTH: 19
<212> TYPE: RNA
<213> ORGANISM: Artificial
<220> FEATURE:
<223> OTHER INFORMATION: an artificially synthesized sequence

<400> SEQUENCE: 29
cauacaaucg ucuuaaguu                                              19

<210> SEQ ID NO 30
<211> LENGTH: 19
```

```
<212> TYPE: RNA
<213> ORGANISM: Artificial
<220> FEATURE:
<223> OTHER INFORMATION: an artificially synthesized sequence

<400> SEQUENCE: 30
cauggucugg uaaaguuaa                                              19

<210> SEQ ID NO 31
<211> LENGTH: 19
<212> TYPE: RNA
<213> ORGANISM: Artificial
<220> FEATURE:
<223> OTHER INFORMATION: an artificially synthesized sequence

<400> SEQUENCE: 31
ggcucaacau uuugaugaa                                              19

<210> SEQ ID NO 32
<211> LENGTH: 19
<212> TYPE: RNA
<213> ORGANISM: Artificial
<220> FEATURE:
<223> OTHER INFORMATION: an artificially synthesized sequence

<400> SEQUENCE: 32
gguucaugcu gaaauggua                                              19

<210> SEQ ID NO 33
<211> LENGTH: 2866
<212> TYPE: DNA
<213> ORGANISM: Homo sapiens
<300> PUBLICATION INFORMATION:
<308> DATABASE ACCESSION NUMBER: GenBank/NM_002907

<400> SEQUENCE: 33
gagtagcgga aagatctgct cgaggcctgg gtgctttggt gtcggagatc cgagagtcgg      60
agatcggaga gtcggacaca ggacagtcgg acaccggaca gtcaaacacc ggagagttag     120
actgggcttc tcggtgggga gaggctctgg gataactact gttacagctt tgaagggtca     180
agggtgtgcg cttttgttt catccttccc tttcctgctg cagggcgagg ccggtctgta      240
gcggatcact cctttcgcc cacacattgg cggaggagaa accggaaagt taatcactgc      300
cctgctctga gaactcgggc ctttaggggc acgttcgcct gctgaccggt cttctgatct     360
ccccattctt ttccatgcag gaggattggc caccaaagcc tgtttattag cagctgccat     420
ttgttgaaag aaatttggat tatttagaa acaaatttgg aaagaaaaag aatggcgtcc      480
gtttcagctc taactgagga actggattct ataaccagtg agctacatgc agtagaaatt     540
caaattcaag aacttacgga aaggcaacaa gagcttattc agaaaaaaaa agtcctgaca     600
aagaaaataa agcagtgttt agaggattct gatgccgggg caagcaatga atatgattct     660
tcacctgccg cttggaataa agaagatttt ccatggtctg gtaaagttaa agatattctg     720
caaaatgtct ttaaactgga aaagttcaga ccacttcagc ttgaaactat taacgtaaca     780
atggctggaa aggaggtatt tcttgttatg cctacaggag gtgaaagag cttatgttac      840 cagttaccag cattatgttc agatggtttt acactcgtca tttgcccatt gatctctctt     900
atggaagacc aattaatggt tttaaaacaa ttaggaattt cagcaaccat gttaaatgct     960
tctagttcta aggagcatgt taaatgggtt catgctgaaa tggtaaataa aaactccgag    1020
ttaaagctga tttatgtgac tccagagaaa attgcaaaaa gcaaaatgtt tatgtcaaga    1080
ctagagaaag cctatgaagc aaggagattt actcgaattg ctgtggatga agttcactgc    1140
```

```
tgtagtcagt ggggacatga tttcagacct gattataagg cacttggtat cttaaagcgg    1200
cagttcccta acgcatcact aattgggctg actgcaactg caacaaatca cgttttgacg    1260
gatgctcaga aaattttgtg cattgaaaag tgttttactt ttacagcttc ttttaatagg    1320
ccaaatctat attatgaggt tcggcagaag ccctcaaaca ctgaagattt tattgaggat    1380
attgtaaagc tcattaatgg gagatacaaa gggcaatcag gaatcatata ttgttttct    1440 cagaaagact ctgaacaagt tacggttagt ttgcagaatc tgggaattca tgcaggtgct    1500
taccatgcca atttggagcc agaagataag accacagttc atagaaaatg gtcagccaat    1560
gaaattcagg tagtagtggc aactgttgca tttggtatgg gaattgataa gccagatgtg    1620
aggtttgtta tccatcattc aatgagtaaa tccatggaaa attattacca agagagtgga    1680
cgtgcaggtc gagatgacat gaaagcagac tgtattttgt actacggctt tggagatata    1740
ttcagaataa gttcaatggt ggtgatgaa aatgtgggac agcagaagct ttatgagatg    1800
gtatcatact gtcaaaacat aagcaaatgt cgtcgtgtgt tgatggctca acattttgat    1860
gaagtatgga actcagaagc atgtaacaaa atgtgcgata actgctgtaa agacagtgca    1920
tttgaaagaa gaacataac agagtactgc agagatctaa tcaagatcct gaagcaggca    1980
gaggaactga atgaaaaact cactccattg aaactgattg attcttggat gggaagggt    2040 gcagcaaaac tgagagtagc aggtgttgtg gctcccacac ttcctcgtga agatctggag    2100
aagattattg cacactttct aatacagcag tatcttaaag aagactacag ttttacagct    2160
tatgctacca tttcgtattt gaaaatagga cctaaagcta accttctgaa caatgaggca    2220
catgctatta ctatgcaagt gacaaagtcc acgcagaact ctttcagggc tgaatcgtct    2280
caaacttgtc attctgaaca aggtgataaa aagatggagg aaaaaaattc aggcaacttc    2340
cagaagaagg ctgcaaacat gcttcagcag tctggttcta agaatacagg agctaagaaa    2400
agaaaaatcg atgatgcctg atatgaatgt tactaaattt tctaattaaa gatggtttat    2460
gcatgtatat gccattattt ttgtagttag acaatagttt ttaaaagaat tcatagata    2520 tttatatgt atggatctat atttcagag cttatctctg aagatctaaa cttttgagaa    2580
tgtttgaaaa ttagagatca tgaattatat aattttccag tataaaacaa gggaaaaatt    2640
tttatgtaaa acccttaaa tgtaaaatat ttgagaataa gttcatacaa tcgtcttaag    2700
ttttttatgc ctttatatac ttagctatat tttttctttt gacataacta tcttttgaa    2760 agcaatatta tactgacaga ggctcactga gtgatacttt aagttaaata tgtagatcaa    2820
gggatgtcca atcttttggc ttccctgagc cagcgaattg tgcaca               2866

<210> SEQ ID NO 34
<211> LENGTH: 2286
<212> TYPE: DNA
<213> ORGANISM: Homo sapiens
<300> PUBLICATION INFORMATION:
<308> DATABASE ACCESSION NUMBER: GenBank/NM_032941

<400> SEQUENCE: 34
gagtagcgga aagatctgct cgaggcctgg gtgctttggt gtcggagatc cgagagtcgg      60
agatcggaga gtcggacaca ggacagtcgg acaccggaca gtcaaacacc ggagagttag     120
actgggcttc tcgtggggga gaggctctgg gataactact gttacagctt tgaagggtca     180
agggaggatt ggccaccaaa gcctgttat tagcagctgc catttgttga agaaatttg       240 gattatttta gaaacaaatt tggaaagaaa agaatggcg tccgtttcag ctctaactga     300
ggaactggat tctataacca gtgagctaca tgcagtagaa attcaaattc aagaacttac    360
```

```
ggaaaggcaa caagagctta ttcagaaaaa aaagtcctg acaaagaaaa taaagcagtg      420
tttagaggat tctgatgccg gggcaagcaa tgaatatgat tcttcacctg ccgcttggaa      480
taaagaagat tttccatggt ctggtaaagt taaagatatt ctgcaaaatg tctttaaact      540
ggaaaagttc agaccacttc agcttgaaac tattaacgta acaatggctg aaaggaggt       600 atttcttgtt atgcctacag gaggtggaaa gagcttatgt taccagttac cagcattatg      660
ttcagatggt tttacactcg tcatttgccc attgatctct cttatggaag accaattaat      720
ggttttaaaa caattaggaa tttcagcaac catgttaaat gcttctagtt ctaaggagca      780
tgttaaatgg gttcatgctg aaatggtaaa taaaaactcc gagttaaagc tgatttatgt      840
gactccagag aaaattgcaa aaagcaaaat gtttatgtca agactagaga aagcctatga      900
agcaaggaga tttactcgaa ttgctgtgga tgaagttcac tgctgtagtc agtggggaca      960
tgatttcaga cctgattata aggcacttgg tatcttaaag cggcagttcc ctaacgcatc     1020
actaattggg ctgactgcaa ctgcaacaaa tcacgttttg acggatgctc agaaaatttt     1080
gtgcattgaa aagtgtttta cttttacagc ttcttttaat aggccaaatc tatattatga     1140
ggttcggcag aagcccctcaa acactgaaga ttttattgag gatattgtaa agctcattaa     1200
tgggagatac aaagggcaat caggaatcat atattgtttt tctcagaaag actctgaaca     1260
agttacggtt agtttgcaga atctgggaat tcatgcaggt gcttaccatg ccaatttgga     1320
gccagaagat aagaccacag ttcatagaaa atggtcagcc aatgaaattc aggtagtagt     1380
ggcaactgtt gcatttggta tgggaattga taagccagat gtgaggtttg ttatccatca     1440
ttcaatgagt aaatccatgg aaaattatta ccaagagagt ggacgtgcag gtcgagatga     1500
catgaaagca gactgtattt tgtactacgg ctttggagat atattcagaa taagttcaat     1560
ggtggtgatg aaaatgtgg gacagcagaa gctttatgag atggtatcat actgtcaaaa      1620
cataagcaaa tgtcgtcgtg tgttgatggc tcaacatttt gatgaagtat ggaactcaga     1680
agcatgtaac aaaatgtgcg ataactgctg taaagacagt gcatttgaaa gaaagaacat     1740
aacagagtac tgcagagatc taatcaagat cctgaagcag gcagaggaac tgaatgaaaa     1800
actcactcca ttgaaactga ttgattcttg gatgggaaag ggtgcagcaa aactgagagt     1860
agcaggtgtt gtggctccca cacttcctcg tgaagatctg gagaagatta ttgcacactt     1920
tctaatacag cagtatctta agaagactaa cagttttaca gcttatgcta ccatttcgta     1980
tttgaaaata ggacctaaag ctaaccttct gaacaatgag gcacatgcta ttactatgca     2040
agtgacaaag tccacgcaga actctttcag ggctgaatcg tctcaaactt gtcattctga     2100
acaaggtgat aaaagatgg aggaaaaaaa ttcaggcaac ttccagaaga aggctgcaaa      2160
catgcttcag cagtctggtt ctaagaatac aggagctaag aaaagaaaaa tcgatgatgc     2220
ctgatatgaa tgttactaaa tttttctaatt aaagatggtt tatgcaaaaa aaaaaaaaa     2280 aaaaaa                                                                2286
```

<210> SEQ ID NO 35
<211> LENGTH: 2251
<212> TYPE: DNA
<213> ORGANISM: Homo sapiens
<300> PUBLICATION INFORMATION:
<308> DATABASE ACCESSION NUMBER: GenBank/BC001052

<400> SEQUENCE: 35

```
ggcacgaggg agatccgaga gtcggagatc ggagagtcgg acacaggaca gtcggacacc       60
ggacagtcaa acaccggaga gttagactgg gcttctcggt ggggagaggc tctgggataa      120
```

```
ctactgttac agctttgaag ggtcaaggga ggattggcca ccaaagcctg tttattagca        180
gctgccattt gttgaaagaa atttggatta ttttagaaac aaatttggaa agaaaaagaa        240
tggcgtccgt ttcagctcta actgaggaac tggattctat aaccagtgag ctacatgcag        300
tagaaattca aattcaagaa cttacggaaa ggcaacaaga gcttattcag aaaaaaaaag        360
tcctgacaaa gaaaataaag cagtgtttag aggattctga tgccggggca agcaatgaat        420
atgattcttc acctgccgct tggaataaag aagattttcc atggtctggt aaagttaaag        480
atattctgca aaatgtcttt aaactggaaa agttcagacc acttcagctt gaaactatta        540
acgtaacaat ggctggaaag gaggtatttc ttgttatgcc tacaggaggt ggaaagagct        600
tatgttacca gttaccagca ttatgttcag atggttttac actcgtcatt tgcccattga        660
tctctcttat ggaagaccaa ttaatggttt taaaacaatt aggaatttca gcaaccatgt        720
taaatgcttc tagttctaag gagcatgtta atgggttca tgctgaaatg gtaaataaaa         780
actccgagtt aaagctgatt tatgtgactc agagaaaat tgcaaaaagc aaaatgttta        840
tgtcaagact agagaaagcc tatgaagcaa ggagatttac tcgaattgct gtggatgaag        900
ttcactgctg tagtcagtgg ggacatgatt tcagacctga ttataaggca cttggtatct        960
taaagcggca gttccctaac gcatcactaa ttgggctgac tgcaactgca acaaatcacg       1020
ttttgacgga tgctcagaaa atttttgtgca ttgaaaagtg ttttacttt acagcttctt       1080
ttaataggcc aaatctatat tatgaggttc ggcagaagcc ctcaaacact gaagatttta       1140
ttgaggatat tgtaaagctc attaatggga gatacaaagg gcaatcagga atcatatat        1200
gtttttctca gaaagactct gaacaagtta cggttagttt gcagaatctg ggaattcatg       1260
caggtgctta ccatgccaat ttggagccag aagataagac cacagttcat agaaaatggt       1320
cagccaatga aattcaggta gtagtggcaa ctgttgcatt tggtatggga attgataagc       1380
cagatgtgag gttgttatc catcattcaa tgagtaaatc catggaaaat tattaccaag        1440
agagtggacg tgcaggtcga gatgacatga aagcagactg tattttgtac tacggctttg       1500
gagatatatt cagaataagt tcaatggtgg tgatggaaaa tgtgggacag cagaagcttt       1560
atgagatggt atcatactgt caaaacataa gcaaatgtcg tcgtgtgttg atggctcaac       1620
attttgatga agtatggaac tcagaagcat gtaacaaaat gtgcgataac tgctgtaaag       1680
acagtgcatt tgaaagaaag aacataacag agtactgcag agatctaatc aagatcctga       1740
agcaggcaga ggaactgaat gaaaaactca ctccattgaa actgattgat tcttggatgg       1800
gaaagggtgc agcaaaactg agagtagcag gtgttgtggc tcccacactt cctcgtgaag       1860
atctggagaa gattattgca cactttctaa tacagcagta tcttaaagaa gactacagtt       1920
ttacagctta tgctaccatt tcgtatttga aaataggacc taaagctaac cttctgaaca       1980
atgaggcaca tgctattact atgcaagtga caaagtccac gcagaactct ttcagggctg       2040
aatcgtctca aacttgtcat tctgaacaag gtgataaaaa gatggagaaa aaaaattcag       2100
gcaacttcca gaagaggct gcaaacatgc ttcagcagtc tggttctaag aatacaggag       2160
ctaagaaaag aaaaatcgat gatgcctgat atgaatgtta ctaaattttc taattaaaga       2220
tggtttatgc aaaaaaaaaa aaaaaaaaa a                                       2251

<210> SEQ ID NO 36
<211> LENGTH: 2449
<212> TYPE: DNA
<213> ORGANISM: Homo sapiens
<300> PUBLICATION INFORMATION:
<308> DATABASE ACCESSION NUMBER: GenBank/D37984
```

<400> SEQUENCE: 36

```
tcggcgtccg tttcagctct aactgaggaa ctggattcta taaccagtga gctacatgca      60
gtagaaattc aaattcaaga acttacggaa aggcaacaag agcttattca gaaaaaaaaa     120
gtcctgacaa agaaaataaa gcagtgttta gaggattctg atgccggggc aagcaatgaa     180
tatgattctt cacctgccgc ttggaataaa aagattttc catggtctgg taaagttaaa      240
gatattctgc aaaatgtctt taaactggaa aagttcagac cacttcagct tgaaactatt     300
aacgtaacaa tggctggaaa ggaggtattt cttgttatgc ctacaggagg tggaaagagc     360
ttatgttacc agttaccagc attatgttca gatggtttta cactcgtcat ttgcccattg     420
atctctctta tggaagacca attaatggtt ttaaaacaat taggaatttc agcaaccatg     480
ttaaatgctt ctagttctaa ggagcatgtt aaatgggttc atgctgaaat ggtaaataaa     540
aactccgagt taaagctgat ttatgtgact ccagagaaaa ttgcaaaaag caaaatgttt     600
atgtcaagac tagagaaagc ctatgaagca aggagattta ctcgaattgc tgtggatgaa     660
gttcactgct gtagtcagtg gggacatgat ttcagacctg attataaggc acttggtatc     720
ttaaagcggc agttccctaa cgcatcacta attgggctga ctgcaactgc aacaaatcac     780
gttttgacgg atgctcagaa aattttgtgc attgaaaagt gttttacttt tacagcttct     840
tttaataggc caaatctata ttatgaggtt cggcagaagc cctcaaacac tgaagatttt     900
attgaggata ttgtaaagct cattaatggg agatacaaag gcaatcagg aatcatatat      960
tgttttctc agaagactc tgaacaagtt acggttagtt tgcagaatct gggaattcat     1020
gcaggtgctt accatgccaa tttggagcca gaagataaga ccacagttca tagaaaatgg     1080
tcagccaatg aaattcaggt agtagtggca actgttgcat ttggtatggg aattgataag     1140
ccagatgtga ggtttgttat ccatcattca atgagtaaat ccatggaaaa ttattaccaa     1200
gagagtggac gtgcaggtcg agatgacatg aaagcagact gtattttgta ctacggcttt     1260
ggagatatat tcagaataag ttcaatggtg gtgatggaaa atgtgggaca gcagaagctt     1320
tatgagatgg tatcatactg tcaaaacata agcaaatgtc gtcgtgtgtt gatggctcaa     1380
cattttgatg aagtatggaa ctcagaagca tgtaacaaaa tgtgcgataa ctgctgtaaa     1440
gacagtgcat ttgaaagaaa gaacataaca gagtactgca gagatctaat caagatcctg     1500
aagcaggcag aggaactgaa tgaaaaactc actccattga aactgattga ttcttggatg     1560
ggaaagggtg cagcaaaact gagagtagca ggtgttgtgg ctcccacact tcctcgtgaa     1620
gatctggaga agattattgc acactttcta atacagcagt atcttaaaga agactacagt     1680
tttacagctt atgctaccat ttcgtatttg aaaataggac ctaaagctaa tcttctgaac     1740
aatgaggcac atgctattac tatgcaagtg acaaagtcca cgcagaactc tttcagggct     1800
gaatcgtctc aaacttgtca ttctgaacaa ggtgataaaa agatggagga aaaaaattca     1860
ggcaacttcc agaagaaggc tgcaaacatg cttcagcaat ctggttctaa gaatacagga     1920
gctaagaaaa gaaaaatcga tgatgcctga tatgactgtt actaaatttt ctaattaaag     1980
atggtttatg catgtatatg ccattatttt tgtagttaga caatagtttt taaaagaatt     2040
tcatagatat tttatatgta tggatctata ttttcagagc ttatctctga agatctaaac     2100
ttttggagaa tgtttggaaa attagagatc atgaattata taattttcca gtataaaaca     2160
agggaaaaat ttttatgtaa aacccttaa atgtaaaata tttgagaata agttcataca     2220
atcgtcttaa gttttttatg cctttatata cttagctata ttttttcttt tgacataacc     2280
atcttttga aagcaatatt atactgacag aggttcactg agtgatactt taagttaaat     2340
```

```
atgtagatca gggatgtcca atcttttggc ttccctgagc cacattggaa gaagaattgt   2400
cttgggccgc acataaaata tgctaacact gacgatagct gatgagctt              2449

<210> SEQ ID NO 37
<211> LENGTH: 2925
<212> TYPE: DNA
<213> ORGANISM: Homo sapiens
<300> PUBLICATION INFORMATION:
<308> DATABASE ACCESSION NUMBER: GenBank/L36140

<400> SEQUENCE: 37
cttttttttt tttttttttt ttttttataag attattagta taaaattttta gataggtagg     60 agtagcgaaa agatctgctc gaggcctggg tgctttggtg tcggagatcc gagagtcgga    120
gatcggagag tcggacacag gacagtcgga caccggacag tcaaacaccg agagttaga     180 ctgggcttct cggtggggac aggctctggg ataactactg ttacagcttt gaagggtcaa    240
gggtgtgcgc ttttctttc atccttccct ttcctgctgc aggcgaggcc ggtctgatgc     300
ggatcacttc ctttcgccca cacattggcg gaggagaaac cggaaagtta atcactgccc    360
tgctctgaga actcgggcct ttaggggcac gttcgcctgc tgaccggtct tctgatctcc    420
ccattctttt ccatgcagga ggattggcca ccaaagcctg tttattagca gctgccattt    480
gttaaagaaa tttggattat tttagaaaca atttggaaag aaaaagaatg gcgtccgttt    540
cagctctaac tgaggaactg gattctataa ccagtgagct acatgcagta gaaattcaaa    600
ttcaagaact tacggaaagg caacaagagc ttattcagaa aaaaaagtc ctgacaaaga    660 aaataaagca gtgtttagag gattctgatg ccggggcaag caatgaatat gattcttcac    720
ctgccgcttg gaataaagaa gatttttccat ggtctggtaa agttaaagat attctgcaaa    780
atgtctttaa actggaaaag ttcagaccac ttcagcttga aactattaac gtaacaatgg    840
ctggaaagga ggtatttctt gttatgccta caggaggtgg aaagagctta tgttaccagt    900
taccagcatt atgttcagat ggttttacac tcgtcatttg cccattgatc tctcttatgg    960
aagaccaatt aatggttttta aaacaattag gaatttcagc aaccatgtta aatgcttcta   1020
gttctaagga gcatgttaaa tgggttcatg atgaaatggt aaataaaaac tccgagttaa   1080
agctgattta tgtgactcca gagaaaattg caaaaagcaa aatgtttatg tcaagactag   1140
agaaagccta tgaagcaagg agatttactc gaattgctgt ggatgaagtt cactgctgta   1200
gtcagtgggg acatgatttc agacctgatt ataaggcact tggtatctta aagcggcagt   1260
tccctaacgc atcactaatt gggctgactg caactgcaac aaatcacgtt ttgacggatg   1320
ctcagaaaat tttgtgcatt gaaaagtgtt ttacttttac agcttctttt aataggccaa   1380
atctatatta tgaggttcgg cagaagccct caaacactga gatttttatt gaggatattg   1440
taaagctcat taatgggaga tacaaagggc aatcaggaat catatattgt ttttctcaga   1500
aagactctga acaagttacg gttagtttgc agaatctggg aattcatgca ggtgcttacc   1560
atgccaattt ggagccagaa gataagacca cagttcatag aaaatggtca gccaatgaaa   1620
ttcaggtagt agtggcaact gttgcatttg gtatgggaat tgataagcca gatgtgaggt   1680
ttgttatcca tcattcaatg agtaaatcca tggaaaatta ttaccaagag agtggacgtg   1740
caggtcgaga tgacatgaaa gcagactgta ttttgtacta cggcttttga gatatattca   1800
gaataagttc aatggtggtg atggaaaatg tgggacagca aagctttat gagatggtat   1860 catactgtca aacataagc aaatctcgtc gtgtgttgat ggctcaacat tttgatgaag   1920
tatggaactc agaagcatgt aacaaaatgt gcgataactg ctgtaaagac agtgcatttg   1980
```

```
aaagaacgaa cataacagag tactgcagag atctaatcaa gatcctgaag caggcagagg    2040
aactgaatga aaaactcact ccattgaaac tgattgattc ttggatggga aagggtgcag    2100
caaaactgag agtagcaggt gttgtggctc ccacacttcc tcgtgaagat ctggagaaga    2160
ttattgcaca ctttctaata cagcagtatc ttaaagaaga ctacagtttt acagcttatg    2220
ctgccatttc gtatttgaaa ataggaccta aagctaatct tctgaacaat gaggcacatg    2280
ctattactat gcaagtgaca aagtccacgc agaactcttt cagggctgaa tcgtctcaaa    2340
cttgtcattc tgaacaaggt gataaaaaga atggaggaaa aaaaattcag gcaacttcca    2400
gaagaaggct gcaaacatgc ttcagcaatc tggttctaag aatacaggag ctaagaaaag    2460
aaaaatcgat gatgcctgat atgaatgtta ctaaattttc taattaaaga tggtttatgc    2520
atgtatatgc cattattttt gtagttagac aatagttttt aaaagaattt catagatatt    2580
ttatatgtat ggatctatat tttcagagct tatctctgaa gatctaaact tttgagaatg    2640
tttgaaaatt agagatcatg aattatataa ttttccagtg taaacaagg gaaaaatttt    2700 tatgtaaaac cctttaaatg taaaatattt gagaataagt tcatacaatc gtcttaagtt    2760
ttttatgcct ttatatactt agctatattt tttcttttga cataactatc tttttgaaag    2820
caatattata ctgacagagg cttcactgag tgatacttta agttaaatat gtagatcaag    2880
ggatgtccaa tcttttggct tccctgagcc agcgaattgt gcaca                    2925
```

<210> SEQ ID NO 38
<211> LENGTH: 649
<212> TYPE: PRT
<213> ORGANISM: Homo sapiens
<300> PUBLICATION INFORMATION:
<308> DATABASE ACCESSION NUMBER: GenBank/NM_002907

<400> SEQUENCE: 38

```
Met Ala Ser Val Ser Ala Leu Thr Glu Glu Leu Asp Ser Ile Thr Ser
1               5                   10                  15

Glu Leu His Ala Val Glu Ile Gln Ile Gln Glu Leu Thr Glu Arg Gln
            20                  25                  30

Gln Glu Leu Ile Gln Lys Lys Val Leu Thr Lys Lys Ile Lys Gln
        35                  40                  45

Cys Leu Glu Asp Ser Asp Ala Gly Ala Ser Asn Glu Tyr Asp Ser Ser
    50                  55                  60

Pro Ala Ala Trp Asn Lys Glu Asp Phe Pro Trp Ser Gly Lys Val Lys
65                  70                  75                  80

Asp Ile Leu Gln Asn Val Phe Lys Leu Glu Lys Phe Arg Pro Leu Gln
                85                  90                  95

Leu Glu Thr Ile Asn Val Thr Met Ala Gly Lys Glu Val Phe Leu Val
            100                 105                 110

Met Pro Thr Gly Gly Gly Lys Ser Leu Cys Tyr Gln Leu Pro Ala Leu
        115                 120                 125

Cys Ser Asp Gly Phe Thr Leu Val Ile Cys Pro Leu Ile Ser Leu Met
    130                 135                 140

Glu Asp Gln Leu Met Val Leu Lys Gln Leu Gly Ile Ser Ala Thr Met
145                 150                 155                 160

Leu Asn Ala Ser Ser Lys Glu His Val Lys Trp Val His Ala Glu
                165                 170                 175

Met Val Asn Lys Asn Ser Glu Leu Lys Leu Ile Tyr Val Thr Pro Glu
            180                 185                 190

Lys Ile Ala Lys Ser Lys Met Phe Met Ser Arg Leu Glu Lys Ala Tyr
```

```
              195                 200                 205
Glu Ala Arg Arg Phe Thr Arg Ile Ala Val Asp Glu Val His Cys Cys
210                 215                 220

Ser Gln Trp Gly His Asp Phe Arg Pro Asp Tyr Lys Ala Leu Gly Ile
225                 230                 235                 240

Leu Lys Arg Gln Phe Pro Asn Ala Ser Leu Ile Gly Leu Thr Ala Thr
                245                 250                 255

Ala Thr Asn His Val Leu Thr Asp Ala Gln Lys Ile Leu Cys Ile Glu
                260                 265                 270

Lys Cys Phe Thr Phe Thr Ala Ser Phe Asn Arg Pro Asn Leu Tyr Tyr
            275                 280                 285

Glu Val Arg Gln Lys Pro Ser Asn Thr Glu Asp Phe Ile Glu Asp Ile
            290                 295                 300

Val Lys Leu Ile Asn Gly Arg Tyr Lys Gly Gln Ser Gly Ile Ile Tyr
305                 310                 315                 320

Cys Phe Ser Gln Lys Asp Ser Glu Gln Val Thr Val Ser Leu Gln Asn
                325                 330                 335

Leu Gly Ile His Ala Gly Ala Tyr His Ala Asn Leu Glu Pro Glu Asp
                340                 345                 350

Lys Thr Thr Val His Arg Lys Trp Ser Ala Asn Glu Ile Gln Val Val
            355                 360                 365

Val Ala Thr Val Ala Phe Gly Met Gly Ile Asp Lys Pro Asp Val Arg
370                 375                 380

Phe Val Ile His His Ser Met Ser Lys Ser Met Glu Asn Tyr Tyr Gln
385                 390                 395                 400

Glu Ser Gly Arg Ala Gly Arg Asp Asp Met Lys Ala Asp Cys Ile Leu
                405                 410                 415

Tyr Tyr Gly Phe Gly Asp Ile Phe Arg Ile Ser Ser Met Val Val Met
            420                 425                 430

Glu Asn Val Gly Gln Gln Lys Leu Tyr Glu Met Val Ser Tyr Cys Gln
            435                 440                 445

Asn Ile Ser Lys Cys Arg Arg Val Leu Met Ala Gln His Phe Asp Glu
450                 455                 460

Val Trp Asn Ser Glu Ala Cys Asn Lys Met Cys Asp Asn Cys Cys Lys
465                 470                 475                 480

Asp Ser Ala Phe Glu Arg Lys Asn Ile Thr Glu Tyr Cys Arg Asp Leu
                485                 490                 495

Ile Lys Ile Leu Lys Gln Ala Glu Glu Leu Asn Glu Lys Leu Thr Pro
            500                 505                 510

Leu Lys Leu Ile Asp Ser Trp Met Gly Lys Gly Ala Ala Lys Leu Arg
            515                 520                 525

Val Ala Gly Val Val Ala Pro Thr Leu Pro Arg Glu Asp Leu Glu Lys
530                 535                 540

Ile Ile Ala His Phe Leu Ile Gln Gln Tyr Leu Lys Glu Asp Tyr Ser
545                 550                 555                 560

Phe Thr Ala Tyr Ala Thr Ile Ser Tyr Leu Lys Ile Gly Pro Lys Ala
                565                 570                 575

Asn Leu Leu Asn Asn Glu Ala His Ala Ile Thr Met Gln Val Thr Lys
                580                 585                 590

Ser Thr Gln Asn Ser Phe Arg Ala Glu Ser Ser Gln Thr Cys His Ser
            595                 600                 605

Glu Gln Gly Asp Lys Lys Met Glu Glu Lys Asn Ser Gly Asn Phe Gln
            610                 615                 620
```

```
Lys Lys Ala Ala Asn Met Leu Gln Gln Ser Gly Ser Lys Asn Thr Gly
625                 630                 635                 640

Ala Lys Lys Arg Lys Ile Asp Asp Ala
                645

<210> SEQ ID NO 39
<211> LENGTH: 19
<212> TYPE: RNA
<213> ORGANISM: Artificial Sequence
<220> FEATURE:
<223> OTHER INFORMATION: An artificially synthesized siRNA sequence

<400> SEQUENCE: 39
uauaucucca aagccguag                                            19

<210> SEQ ID NO 40
<211> LENGTH: 19
<212> TYPE: RNA
<213> ORGANISM: Artificial
<220> FEATURE:
<223> OTHER INFORMATION: An artificially synthesized siRNA sequence

<400> SEQUENCE: 40
gcuugaaacu auuaacgua                                            19

<210> SEQ ID NO 41
<211> LENGTH: 19
<212> TYPE: RNA
<213> ORGANISM: Artificial
<220> FEATURE:
<223> OTHER INFORMATION: An artificially synthesized siRNA sequence

<400> SEQUENCE: 41
uaagaccaca guucauaga                                            19

<210> SEQ ID NO 42
<211> LENGTH: 19
<212> TYPE: RNA
<213> ORGANISM: Artificial
<220> FEATURE:
<223> OTHER INFORMATION: An artificially synthesized siRNA sequence

<400> SEQUENCE: 42
guuauccauc auucaauga                                            19

<210> SEQ ID NO 43
<211> LENGTH: 27
<212> TYPE: RNA
<213> ORGANISM: Artificial
<220> FEATURE:
<223> OTHER INFORMATION: an artificially synthesized nucleotide sequence

<400> SEQUENCE: 43
ggaaaaguuc agaccacuuc agcuuga                                   27
```